United States Patent
Krauss

(10) Patent No.: US 10,413,535 B2
(45) Date of Patent: Sep. 17, 2019

(54) PHARMACEUTICAL COMPOSITIONS COMPRISING AN INTEGRIN ALPHA4 ANTAGONIST FOR USE IN TREATING OCULAR INFLAMMATORY CONDITIONS

(71) Applicant: AXEROVISION, INC., Carlsbad, CA (US)

(72) Inventor: Achim H. Krauss, San Marcos, CA (US)

(73) Assignee: AXEROVISION, INC., Carlsbad, CA (US)

(*) Notice: Subject to any disclaimer, the term of this patent is extended or adjusted under 35 U.S.C. 154(b) by 0 days.

(21) Appl. No.: 15/742,867

(22) PCT Filed: Jul. 7, 2016

(86) PCT No.: PCT/IB2016/054073
§ 371 (c)(1),
(2) Date: Jan. 8, 2018

(87) PCT Pub. No.: WO2017/006272
PCT Pub. Date: Jan. 12, 2017

(65) Prior Publication Data
US 2018/0200240 A1 Jul. 19, 2018

Related U.S. Application Data

(60) Provisional application No. 62/189,813, filed on Jul. 8, 2015.

(51) Int. Cl.
| | | |
|---|---|---|
| *A61K 31/445* | (2006.01) | |
| *A61K 31/196* | (2006.01) | |
| *A61K 31/192* | (2006.01) | |
| *A61K 45/06* | (2006.01) | |
| *A61K 9/48* | (2006.01) | |
| *A61K 9/06* | (2006.01) | |
| *A61K 9/08* | (2006.01) | |
| *A61K 31/573* | (2006.01) | |
| *A61K 38/13* | (2006.01) | |
| *A61K 9/00* | (2006.01) | |
| *A61P 27/04* | (2006.01) | |

(52) U.S. Cl.
CPC .......... *A61K 31/445* (2013.01); *A61K 9/0048* (2013.01); *A61K 9/06* (2013.01); *A61K 9/08* (2013.01); *A61K 45/06* (2013.01); *A61P 27/04* (2018.01); *A61K 31/192* (2013.01); *A61K 31/196* (2013.01); *A61K 31/573* (2013.01); *A61K 38/13* (2013.01); *A61K 2300/00* (2013.01)

(58) Field of Classification Search
CPC .. A61K 31/445; A61K 31/192; A61K 31/196; A61K 45/06; A61K 9/06; A61K 9/08; A61K 9/48; A61P 27/04; A61P 29/00
See application file for complete search history.

(56) References Cited

U.S. PATENT DOCUMENTS

| | | | |
|---|---|---|---|
| 6,867,192 B1 | 3/2005 | Armour et al. | |
| 2006/0281739 A1* | 12/2006 | Gadek | A61K 31/198 514/227.5 |
| 2007/0105761 A1 | 5/2007 | Chappell et al. | |
| 2013/0217657 A1 | 8/2013 | Lindstrom et al. | |

FOREIGN PATENT DOCUMENTS

| | | |
|---|---|---|
| WO | WO-2001/95879 | 12/2001 |
| WO | WO-2006/125119 | 11/2006 |

OTHER PUBLICATIONS

Ecoiffier et al. "Role of Alpha-4 Beta-1 Integrin (VLA-4) in Dry Eye Syndrome" May 2007, Investigative Ophthalmology & Visual Science, vol. 48, p. 2308; abstract (Year: 2007).*

Andonian, "Ocular and systemic pharmacokinetics of GW559090, an Alpha-4 integrin antagonist, in mouse, rabbit and dog following topical administration," Arvo Annual Meeting Abstract (2015) Retrieved on Jun. 26, 2018. Retrieved on http://iovs.arvojournals.org/article.aspx?articleid=2334394.

Contrerars-Ruiz et al. "Sjogren's syndrome associated dry eye in a mouse model is ameliorated by topical application on integrin [alpha]4 antagonist GW559090," Experimental Eye Research (2015) 143:1-8.

International Search Report for PCT/IB2016/054073, dated Sep. 6, 2016, 6 pages.

Krauss et al., "Effects of a novel integrin antagonist, GW559090, in an experimental dry eye model (Program No. 2472)," ARVO (2015) Abstract.

Krauss et al., "Improvement of outcome measures of dry eye by a novel integrin antagonist in the murine desiccating stress model," Investigative ophthalmology & visual science (2015) AOPT 12th Scientific Meeting. Poster Board #50. Abstract.

Krauss et al., "Improvement of outcome measures of dry eye by a novel integrin antagonist in the murine desiccating stress model," Investigative ophthalmology & visual science (2015) 56(10):5888-5895.

Miscellaneous, "An inhaled VLA-4 antagonist," Expert Opinion on Therapeutic Patents (2002) p. 755-757.

* cited by examiner

*Primary Examiner* — Kendra D Carter
(74) *Attorney, Agent, or Firm* — Morrison & Foerster LLP

(57) ABSTRACT

The invention relates to antagonists of integrin α4 and their use in pharmaceutical compositions, primarily topically administered ophthalmic compositions. The pharmaceutical compositions are useful for treating ocular inflammatory conditions, such as dry eye disease, non-infectious uveitis (e.g., anterior, intermediate, posterior, pan-uveitis), non-infectious conjunctivitis, iritis, or scleritis in animals, and particularly mammals, including humans.

15 Claims, 6 Drawing Sheets

PHARMACEUTICAL COMPOSITIONS COMPRISING AN INTEGRIN ALPHA4 ANTAGONIST FOR USE IN TREATING OCULAR INFLAMMATORY CONDITIONS

CROSS REFERENCE TO RELATED APPLICATIONS

This patent application is a U.S. National Phase Application of International Application No. PCT/IB2016/054073, filed Jul. 7, 2016, which claims priority to U.S. Provisional Patent Application No. 62/189,813 filed Jul. 8, 2015, the entire text of which is hereby incorporated by reference into this patent application.

FIELD OF THE INVENTION

This invention relates a pharmaceutical composition, such as a topical ophthalmic composition, comprising an integrin α4 antagonist for use in treating ocular inflammatory conditions, including dry eye disease. This invention also relates to a method for treating ocular inflammatory conditions, including dry eye disease, in humans and other mammals by administering a pharmaceutical composition, such as a topical ophthalmic composition, comprising an integrin α4 antagonist.

BACKGROUND OF THE INVENTION

Dry eye disease (DED) is one of the most common and discomforting eye disorders. It has been defined as a multifactorial ocular surface disease more prevalent in women and the elderly. DED is associated with symptoms of discomfort, visual disturbance, tear film instability and inflammation of the ocular surface leading to potential damage to the ocular surface tissues (Research in Dry Eye DEWS Report 2007). The pro-inflammatory milieu is characterized by increased levels of cytokines and chemokines in the tear film, cornea and conjunctiva, and increased autoreactive T-cell infiltration of the conjunctival epithelium and sometimes lacrimal gland (Pflugfelder et al., 1999; de Paiva et al., 2009a; Massingale et al., 2009); as reviewed by Stern and colleagues (Stern et al., 2010; Stern et al., 2013). Alteration of the tear film composition (mucins, lipids, proteins) and decreased volume lead to tear film abnormalities that contribute to the disease cycle.

Subjecting mice to a controlled environment of desiccating stress (DS) results in ocular surface pathology reminiscent of human DED in patients in many respects (Dursun et al., 2002; de Paiva et al., 2006b; Niederkorn et al., 2006; de Paiva et al., 2009a). As of today, this model represents the best characterized animal model to study DED.

Integrins are heterodimeric glycoproteins consisting of one α- and one β-subunit. Expressed on the cell surface of leukocytes, integrins play a role in their recruitment to sites of inflammation. The association of a specific α- and β-subunit determines the ligand specificity of the integrin. The α4 integrin subunit (CD49d) is a constituent of Very Late Antigen-4, VLA-4 (integrin α4β1; CD49d/CD29) and α4β7 (CD49d/CD103). In the case of integrin α4β1, the corresponding ligands are the immunoglobulin superfamily adhesion molecule vascular cell adhesion molecule 1 (VCAM-1) on vascular endothelial cells and the extracellular matrix glycoprotein fibronectin, which are responsible for the homing, trafficking, differentiation, priming, activation, proliferation and survival of integrin α4β1 expressing cells. Integrin α4β1 is expressed on lymphocytes, monocytes, macrophages, NK cells and eosinophils. Integrin α4β7 and its corresponding ligand, MAdCAM (Mucosal Addressin Cell Adhesion Molecule-1), regulate leukocyte trafficking to the gut, but their involvement in DED cannot be ruled out.

Natalizumab, an antibody directed against the integrin α4 subunit, has been shown to profoundly inhibit inflammation and improve clinical outcomes in both multiple sclerosis (Cross and Naismith, 2014) and Crohn's disease (Cohen et al., 2014) which are also T cell mediated pathologies. Lifitegrast, a small molecule antagonist, directed against a different adhesion molecule (LFA-1, integrin αLβ2), has been shown to reduce corneal staining and improve symptoms when delivered topically to dry eye patients (Sheppard et al., 2014). Furthermore, a specific small molecule antagonist to integrin α4β1, BIO-8809, had been shown to decrease corneal fluorescein staining, conjunctival T cell infiltrates and TNFα expression in cornea and conjunctiva in a murine dry eye model (Ecoiffier et al., 2008). Taken together these considerations provided a rationale for further exploring the blockade of integrin α4 in an animal model of DED.

SUMMARY OF THE INVENTION

In one aspect, the present application is directed to a method for treating an ocular inflammatory condition in a mammal in need thereof, comprising ocularly administering to the mammal a therapeutically effective amount of a compound of formula I

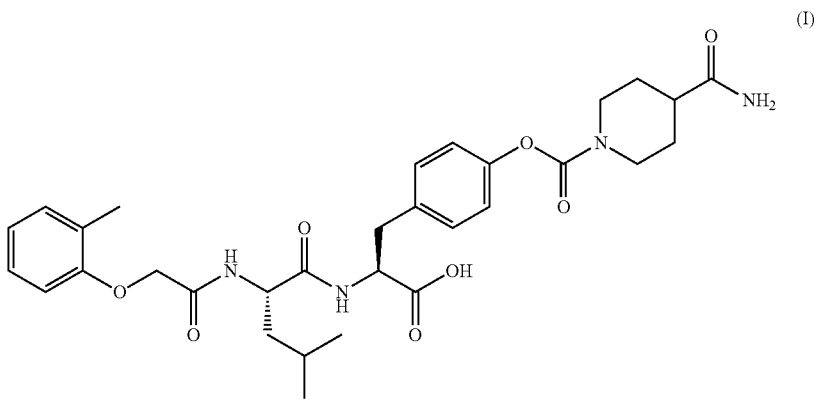 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or a pharmaceutically acceptable salt, ester, anhydride, hydrate, solvate, polymorph, optical isomer, racemate, diastereoisomer or enantiomer thereof (collectively referred to as therapeutic agent A). In certain embodiments, therapeutic agent A is applied topically. Topical administration may be to the cornea, the conjunctival sac, and/or the eyelid. In certain other embodiments, therapeutic agent A is applied locally, e.g., subconjunctivally, intracamerally, intravitreally, subtenon, subretinally, subchoroidally, or suprachoroidally.

In another aspect, the present application is directed to a compound of formula I

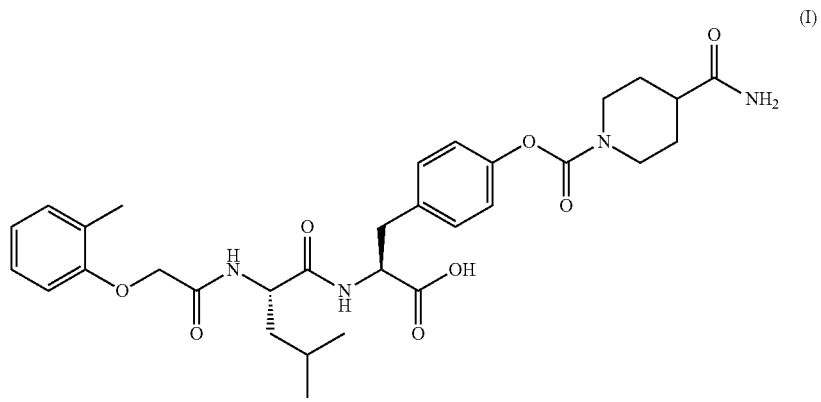 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

(I)

or a pharmaceutically acceptable salt, ester, anhydride, hydrate, solvate, polymorph, optical isomer, racemate, diastereoisomer or enantiomer thereof (collectively referred to as therapeutic agent A) for use in treating an ocular inflammatory condition. In certain embodiments, therapeutic agent A is provided in a pharmaceutically acceptable vehicle, such as a pharmaceutically acceptable ophthalmic vehicle.

In another aspect, the present application is directed to a pharmaceutical composition comprising a compound of formula I

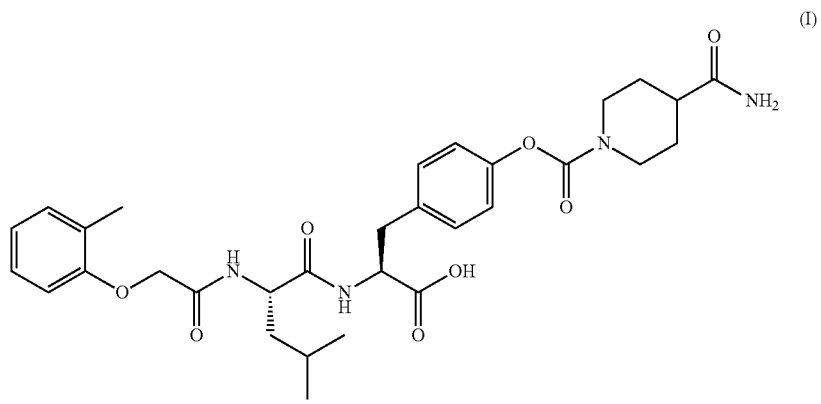 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

(I)

or a pharmaceutically acceptable salt, ester, anhydride, hydrate, solvate, polymorph, optical isomer, racemate, diastereoisomer or enantiomer thereof (collectively referred to as therapeutic agent A) and one or more pharmaceutically acceptable excipients, wherein the composition is useful for treating an ocular inflammatory condition. In certain embodiments, the pharmaceutical composition is suitable for ocular administration. In some such embodiments, the pharmaceutical composition is suitable to be applied topically. In certain embodiments, the pharmaceutical composition is suitable to be applied to the conjunctival sac or to the eyelid. In certain other embodiments, the pharmaceutical composition is suitable to be applied subconjunctivally, intracamerally, intravitreally, subtenon, subretinally, subchoroidally, or suprachoroidally.

In another aspect, the present application is directed to a pharmaceutical composition comprising therapeutic agent A and one or more pharmaceutically acceptable excipients, wherein the composition is useful for treating an ocular inflammatory condition when applied in the form of an eye drop, spray or mist.

In a further aspect, the present application is directed to a pharmaceutical composition comprising therapeutic agent A and one or more pharmaceutically acceptable excipients, wherein the composition is useful for treating an ocular inflammatory condition when applied as a topical ophthalmic formulation.

In still yet another aspect, the present application is directed to a method for treating an ocular inflammatory condition in a mammal (which mammal may be a human) in need thereof by preventing or reducing the migration of antigen-presenting cells to the lymph nodes. Such method comprises administering to said mammal (which mammal may be a human) a therapeutically effective amount of therapeutic agent A.

In another aspect, the present application is directed to a pharmaceutical composition comprising a compound of formula I

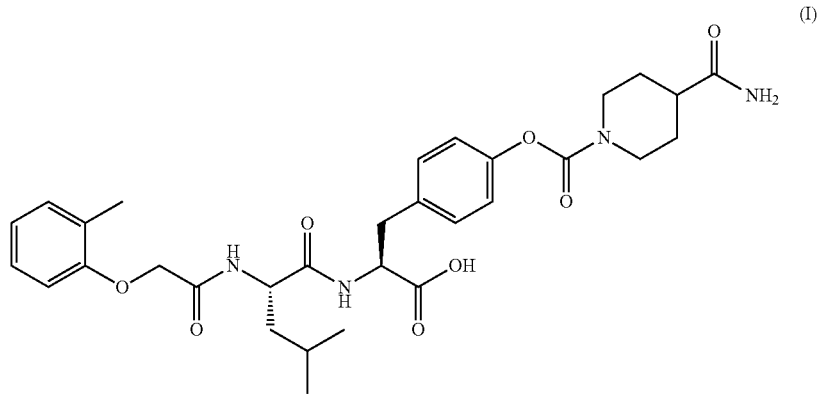 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or a pharmaceutically acceptable salt, ester, anhydride, hydrate, solvate, polymorph, optical isomer, racemate, diastereoisomer or enantiomer thereof and one or more pharmaceutically acceptable excipients.

In yet another aspect, the present application is directed to a method for treatment of an ocular inflammatory condition, such as DED, in a mammal (which mammal may be a human) in need thereof comprising administering to said mammal/human a therapeutically effective amount of: (a) a pharmaceutical composition comprising therapeutic agent A; (b) cyclosporin A; and (c) one or more pharmaceutically acceptable excipients.

In still yet another aspect, the present application is directed to a method for treatment of an ocular inflammatory condition, such as DED, in a mammal (which mammal may be a human) in need thereof comprising administering to said mammal/human a therapeutically effective amount of: (a) a pharmaceutical composition comprising therapeutic agent A; (b) a topical steroid selected from the group consisting of dexamethasone base and phosphate, difluprednate, fluocinolone, fluorometholone base and acetate, loteprednol, prednisolone acetate and phosphate, rimexolone, and triamcinolone acetonide; and (c) one or more pharmaceutically acceptable excipients.

In yet a further aspect, the present application is directed to a method for treatment of an ocular inflammatory condition, such as DED, in a mammal (which mammal may be a human) in need thereof comprising administering to said mammal/human a therapeutically effective amount of: (a) a pharmaceutical composition comprising therapeutic agent A; (b) a non-steroidal anti-inflammatory drug selected from the group consisting of bromfenac, diclofenac, flurbiprofen, ketorolac, and nepafenac; and (c) one or more pharmaceutically acceptable excipients.

In still yet a further aspect, the present application is directed to a method for treatment of an ocular inflammatory condition, such as DED, in a mammal (which mammal may be a human) in need thereof comprising administering to said mammal/human a therapeutically effective amount of: a) a pharmaceutical composition comprising therapeutic agent A; (b) an LFA-1 integrin antagonist such as lifitegrast; and (c) one or more pharmaceutically acceptable excipients.

In yet another aspect, the present application is directed to the use of a compound of formula I

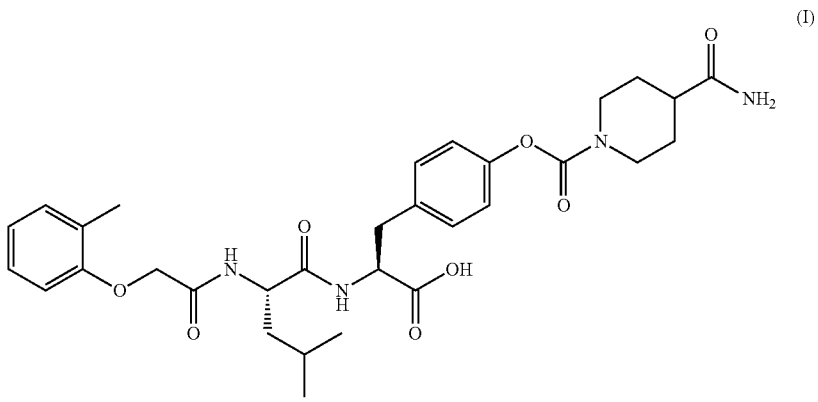 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or a pharmaceutically acceptable salt, ester, anhydride, hydrate, solvate, polymorph, optical isomer, racemate, diastereoisomer or enantiomer thereof in the manufacture of a medicament for the treatment of an ocular inflammatory condition.

In certain embodiments of any of the aforementioned aspects, the ocular inflammatory condition is dry eye disease. In other embodiments of each aspect, the ocular inflammatory condition is non-infectious uveitis (anterior, intermediate, posterior, pan), non-infectious conjunctivitis, iritis, or scleritis.

In certain embodiments of any of the aforementioned aspects, therapeutic agent A is compound (I) or a pharmaceutically acceptable salt thereof. In certain embodiments, therapeutic agent A is the potassium salt of compound (I).

It will be understood by the skilled artisan that any of the preceding methods of treatment and/or uses can be accomplished by the topical or other ocular administration of a pharmaceutical composition containing therapeutic agent A. The term "topical administration" as used herein includes application in the form of an eye drop, spray, mist, gel, cream or ointment applied to the surface of the eye, application to the conjunctival sac, application via an insert, application via a drug delivery device designed to deliver ophthalmic medications, and the like. The term "other ocular administration" as used herein includes subconjunctival, intracameral, intravitreal, subtenon, subretinal, subchoroidal, or suprachoroidal application of a pharmaceutically acceptable formulation, insert or device designed to deliver ophthalmic medications, and the like.

Based on the data presented herein, it is expected that blockade of α4 integrin receptors will treat and ameliorate other ocular inflammatory and immunological conditions whose pathogenesis involves leukocytes, such as all forms of uveitis (anterior, intermediate, posterior, pan), conjunctivitis, iritis, or scleritis (diffuse, nodular, necrotizing) in addition to DED.

The compound of formula I, which is also known as(S)-3-(4-((4-carbamoylpiperidine-1-carbonyl)oxy)phenyl)-2-((S)-4-methyl-2-(2-(o-tolyloxy)acetamido)pentanamido) propanonic acid; or (2S)-3-[4-({[4-(Aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid; or GW559090, is a potent integrin α4 antagonist which had previously been clinically investigated in asthma patients by the oral inhalation route (Ravensberg et al., 2006).

Without being bound to any mechanistic theory of action, the effect of the compound of formula I appears to be both anti-inflammatory and disease modifying. When administered locally to the eye, the compound of formula I improved the corneal epithelial barrier function, decreased inflammatory markers in the cornea and conjunctiva, reduced the recruitment and homing of T lymphocytes to the conjunctiva, and, surprisingly, blocked the migration and activation of antigen-presenting cells to the draining lymph nodes in a murine model of DED. The compound of formula I was ineffective when administered systemically. This is surprising in light of the well-known role of integrins in leukocyte trafficking. If blockade of leukocyte trafficking was the sole, or at least primary, mechanism of action of an integrin α4 antagonist such as the compound of formula I, it can be reasoned that systemic drug exposure should be more important than drug exposure at the ocular surface. Leukocyte trafficking is inhibited by an integrin α4 antagonist bound to circulating leukocytes before they transmigrate the vascular endothelial wall at sites of inflammation through interaction with the cell adhesion molecules VCAM-1 and MAdCAM. The fact that the topical route of administration of the compound of formula I, but not the systemic route, was effective in treating signs of DED in this animal model suggests a local rather than systemic effect by integrin α4 antagonism. This local effect appears to be specific to the integrin α4 antagonist the compound of formula I and differentiated from topical steroid treatment (dexamethasone phosphate) in that topical dexamethasone phosphate ameliorated the DED associated corneal staining, but not the migration of antigen-presenting cells to the draining lymph nodes. It can be appreciated by one of skill in the art from those considerations that the therapeutic effect of integrin α4 antagonism employs a unique mechanism. An important and disease-modifying aspect of this unique mechanism is the interruption of the immune cycle, present in DED, at the draining lymph node level, a mechanism not shared with other drugs, such as topical steroids.

Geometric mean±95% confidence intervals of intensity score of OGD uptake after 5 days of desiccating stress (DS). NS=non-stressed untreated; DS5=desiccating stress for 5 days without topical treatment; all other groups are DS5 with topical treatment; Dex=Dexamethasone phosphate 0.1%; BSS=Balanced Salt Solution (Leiter's Pharmacy, San Jose, Calif.), vehicle for dexamethasone; V GW=phosphate-buffered saline, pH 7 (vehicle for GW559090); GW_1 mg/mL=GW559090 (1 mg/mL); GW_3 mg/mL=GW559090 (3 mg/mL); GW_10 mg/mL=GW559090 (10 mg/mL); GW_30 mg/mL=GW559090 (30 mg/mL). N=26-30. *p<0.05; **p<0.01 compared to control (DS5 vs NS; Dex vs Dex vehicle; GW vs GW vehicle; mixed effects ANOVA of Log 10 OGD data).

Figure 2:
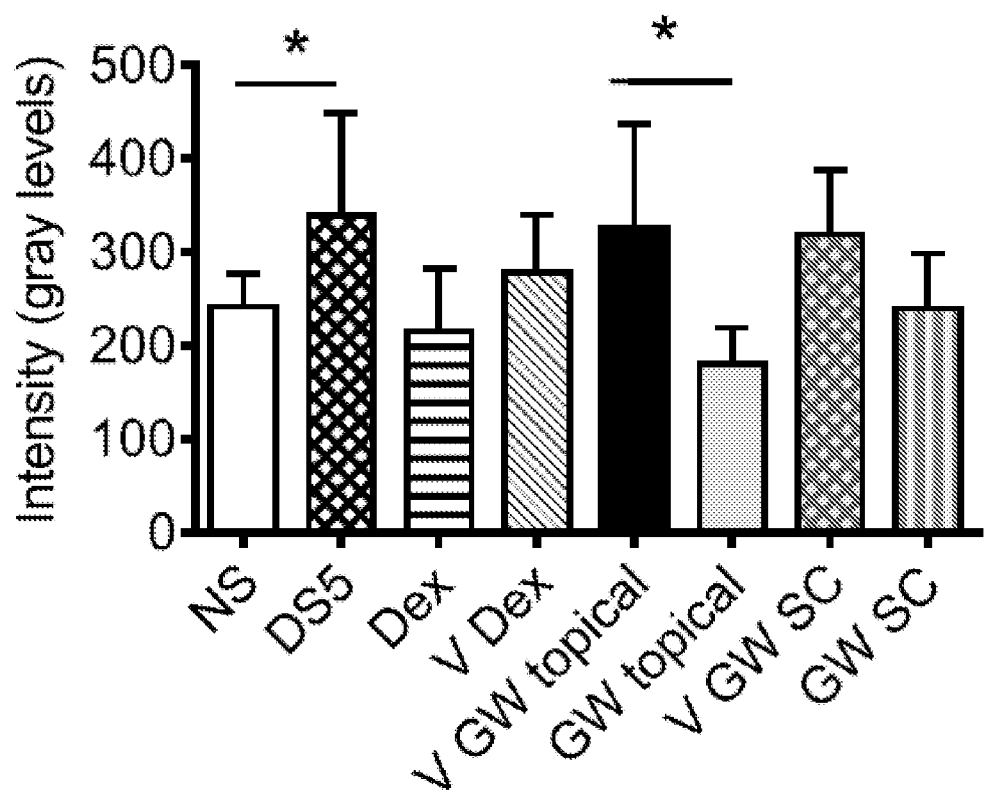

FIG. 2: shows that the compound of formula I acts primarily locally, not systemically, to improve DS-induced corneal barrier disruption.

Geometric mean±95% confidence intervals of intensity score of OGD uptake after 5 days of desiccating stress (DS). NS=non-stressed untreated; DS5=desiccating stress for 5 days without treatment; all other groups are DS5 with treatment; Dex=Dexamethasone phosphate 0.1%; V Dex=Balanced Salt Solution (Leiter's Pharmacy, San Jose, Calif.), vehicle for dexamethasone; GW topical=topical GW559090 (30 mg/mL; 60 μg per eye); GW SC=subcutaneous GW559090 (30 mg/mL; 120 μg); V GW=phosphate-buffered saline, pH 7 (vehicle for GW559090). N=26-30.

*p<0.05; **p<0.01 compared to control (DS5 vs NS; GW vs GW vehicle; mixed effects ANOVA of Log 10 OGD data).

Figure 3A:
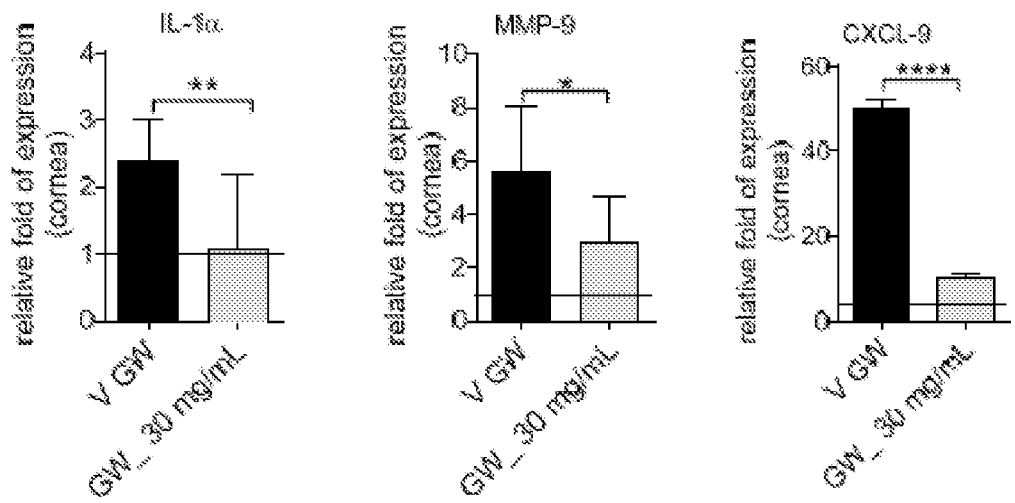
Figure 3B:
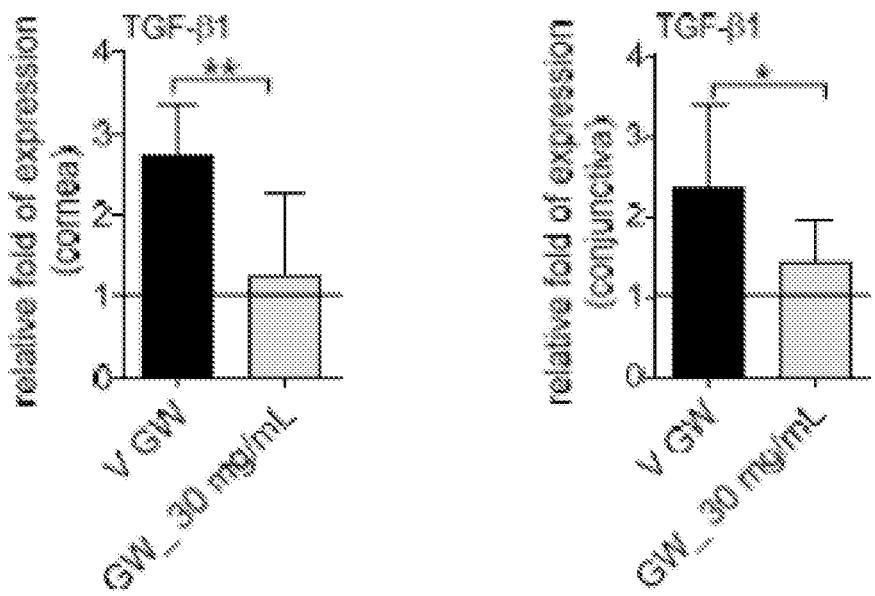

FIG. 3A and FIG. 3B: show that topical treatment with the compound of formula I decreases inflammatory markers.

FIG. 3A. Relative fold of expression±SD of IL-1a, MMP-9, CXCL-9, TGF-b1 genes in cornea FIG. 3B. Relative fold of expression±SD of TGF-b1 gene in conjunctiva Line indicates non-stressed, untreated control.

V GW=phosphate-buffered saline, pH 7 (vehicle); GW_30 mg/mL=GW559090 (30 mg/mL).

N=7-8.

*p<0.05; p<0.01; *p<0.001; ****p<0.0001 (Unpaired T test)

Figure 4:
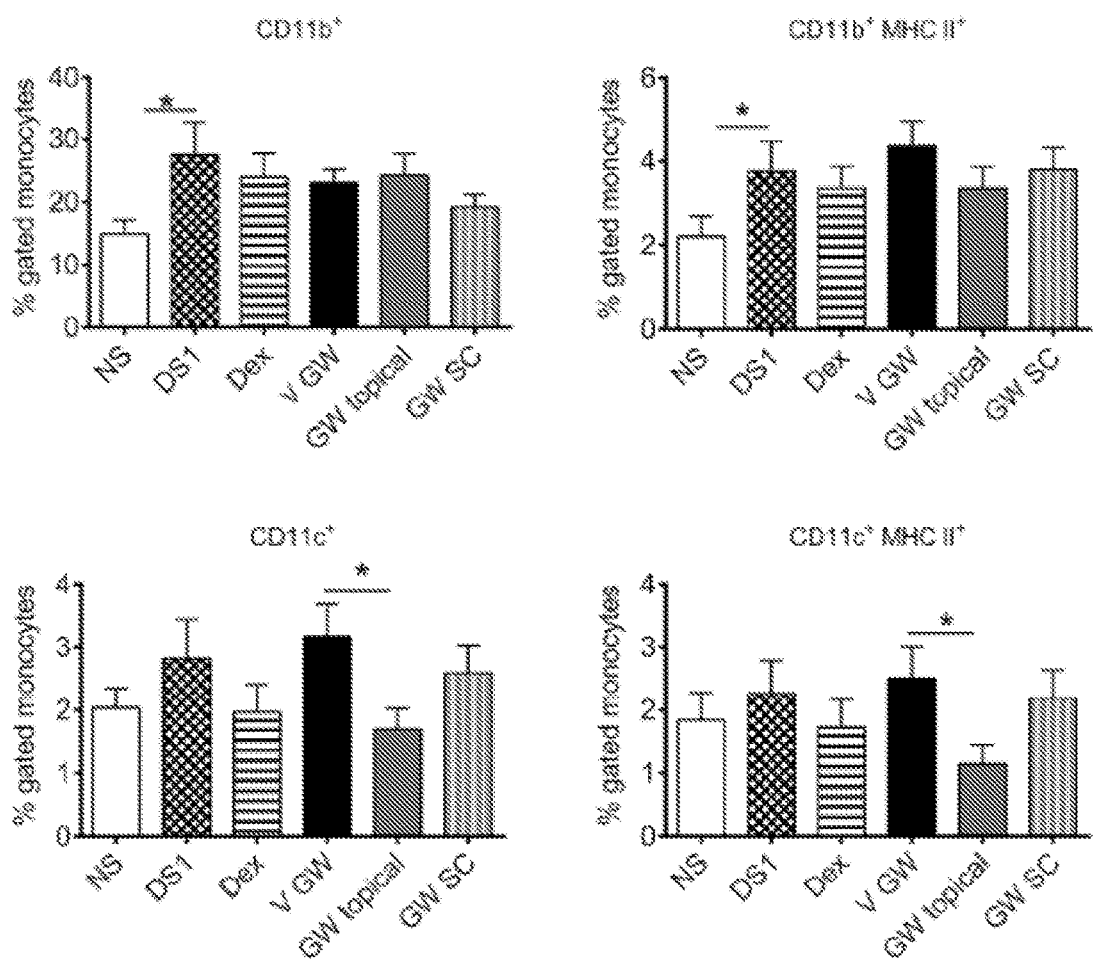

FIG. 4: shows that topical treatment with the compound of formula I decreases CD11c+ and CD11c+/MHC II+ dendritic cells in draining cervical lymph nodes.

Percent gated cells (FACS) isolated from draining CLN which were pooled from each mouse were stained for CD11c, CD11b and MHC II. NS=non-stressed untreated; DS1=desiccating stress for 1 day without treatment; all other groups are DS1 with treatment; Dex=Dexamethasone phosphate 0.1%; V GW=phosphate-buffered saline, pH 7 (vehicle for dexamethasone and GW559090); GW topical=topical bilateral GW559090 (30 mg/mL; 60 µg per eye); GW SC=GW559090 SC BID (30 mg/mL; 120 µg). N=16. *p<0.05; compared to control (DS1 vs NS; GW vs GW vehicle; 2-way ANOVA with fixed treatment and random experiment effects followed by Dunnett's multiple comparison procedure).

Figure 5:
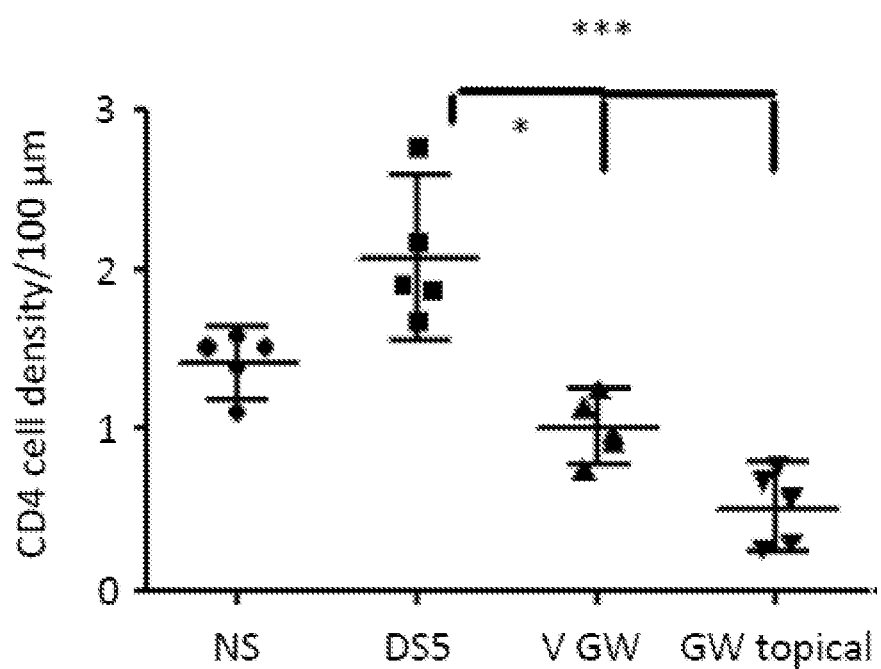

FIG. 5: shows that topical treatment with the compound of formula I decreases conjunctival T cell infiltration.

Cell density group means and 95% confidence intervals after 5 days of desiccating stress (DS). NS=non-stressed untreated; DS5=desiccating stress for 5 days without treatment; all other groups are DS5 with treatment; GW topical=topical GW559090 (30 mg/mL; 60 µg per eye); V GW=phosphate-buffered saline, pH 7 (vehicle for GW559090). N=5.

*p<0.05; ***p<0.001 compared to DS5 control (Kruskal-Wallis procedure, followed by Dunn's multiple comparisons procedure).

Figure 6:
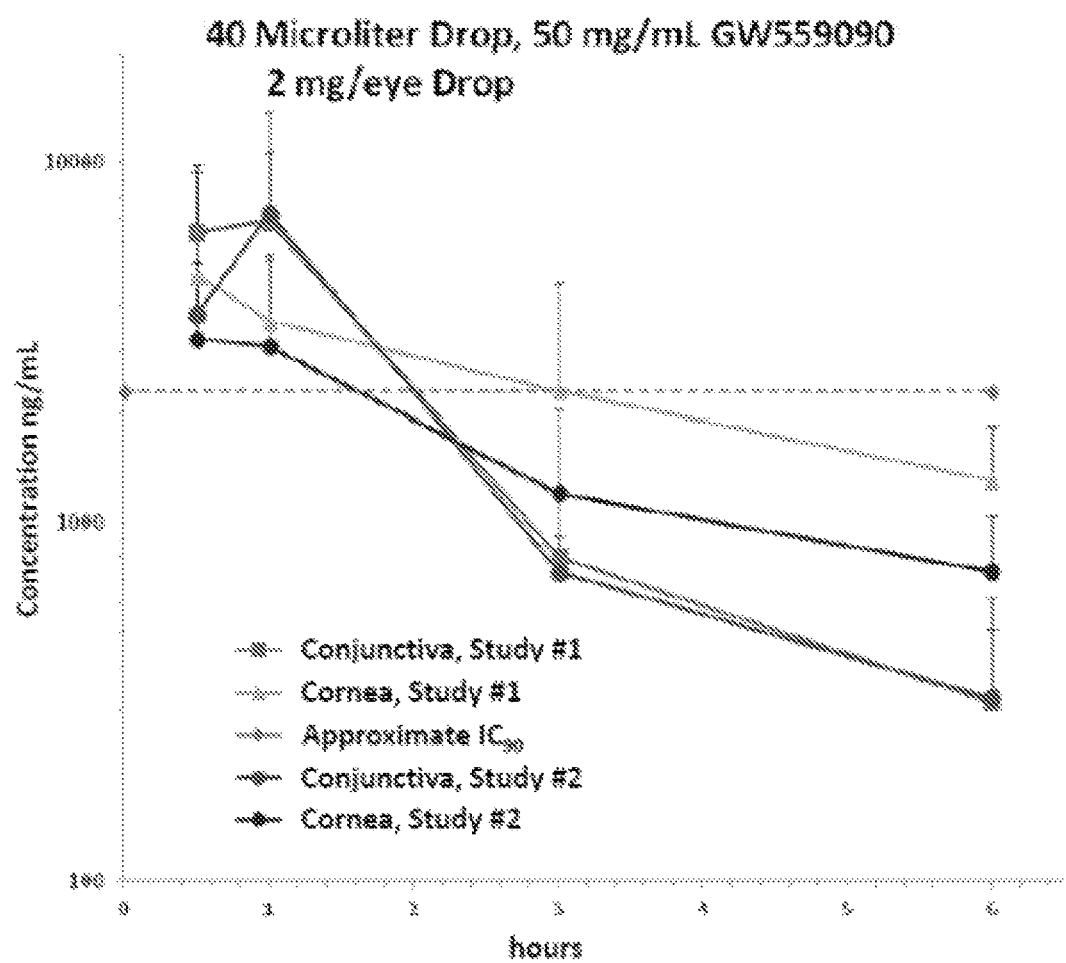

FIG. 6: shows conjunctival and corneal tissue concentrations of GW559090 following administration of 40 µL (50 mg/mL) GW559090A. The dashed line at approximately 4000 nM (~2400 ng/mL) indicates the approximate tissue level required to achieve the IC90 concentration of ~80 nM (~48 ng/mL) if protein binding is 98%. The approximate tissue level required to achieve the 1050 concentration of ~8 nM (~5 ng/mL) if protein binding is 98% is 400 nM (~240 ng/mL). After administration of 40 µL (50 mg/mL) GW559090A, the conjunctival and corneal tissue concentrations are in excess of 3000 ng/mL at 30 minutes and levels persisted above 1000 ng/mL in corneal tissue at 3 hours.

DETAILED DESCRIPTION OF THE INVENTION

I. Local Action of α4 Integrin Antagonist in Murine Model of DED

DED is a multifactorial ocular surface disease that is associated with symptoms of discomfort, visual disturbance, tear film instability and inflammation of the ocular surface leading to potential damage to the ocular surface tissues (Research in Dry Eye DEWS Report 2007). It encompasses a diverse spectrum of etiologies, such as environmental, drug-induced, contact lens wear, aging. DED can also represent an ocular manifestation secondary to a systemic autoimmune condition, such as, but not limited to, Sjögren's syndrome, rheumatoid arthritis, systemic lupus erythematosus, graft versus host disease, Stevens-Johnson syndrome, ocular cictricial pemphigoid, sarcoidosis (reviewed by Stern et al., 2010; Zoukhri, 2006).

As an inflammatory disease of the ocular surface DED is mediated by autoreactive T cells and is associated with corneal barrier dysfunction, increased expression and levels of inflammatory cytokines and chemokines, tear film instability and discomfort. The inventor found that an integrin α4 antagonist, when administered locally to the eye, rescued the corneal epithelial barrier function, decreased inflammatory marker expression in the cornea and conjunctiva, reduced conjunctival T cell infiltration and inhibited the migration and activation of antigen-presenting cells to the draining lymph nodes in a murine model of DED. Primed and activated T lymphocytes traffic from the bloodstream to sites of inflammation with the help of adhesion receptors expressed at their cell surface that interact with corresponding adhesion molecules on the vascular endothelium. Lymphocytic integrins α4β1 (VLA-4), α4β7 and αLβ2 (LFA-1) bind to endothelial VCAM-1, MAdCAM and ICAM-1, respectively. At sites of inflammation, lymphocytic integrin receptors can interact with certain tissue components, fibronectin in the case of α4β1, which further aids in lymphocyte homing, activation and proliferation (Nojima et al., 1990; Cox et al., 2010). The compound of formula I has high-affinity for α4β1 (Table 1). In cell adhesion assays it potently blocked cell adhesion of α4β1 to VCAM-1 and fibronectin (CS-1 domain), as well as α4β7 to MAdCAM (Table 1). The latter interaction is of relevance in the gut environment but has not been studied in the eye. In Sjögren's patients, who have xerostomia and DED, integrin α4β1 has been detected in T lymphocytic infiltrates in labial tissue and VCAM-1 on vascular and dendritic cells (Edwards et al., 1993).

Increased uptake of fluorescent dyes by the corneal epithelium is a hallmark of DED. It has been previously reported that corneal staining intensity with Oregon-Green Dextran (OGD) in mice positively correlates with a reduction in corneal barrier function after experimental DS (de Paiva et al., 2009a; de Paiva et al., 2006b). This mimics what is observed clinically in dry eye patients in whom it is demonstrated by fluorescein staining of the cornea. Low staining scores are indicative of dye exclusion, i.e. corneal barrier integrity. In contrast, high staining scores are reflective of barrier dysfunction. Corneal fluorescein staining scores have been used as important endpoints for diagnosis of DED and as an efficacy parameter in clinical trials.

Figure 1:
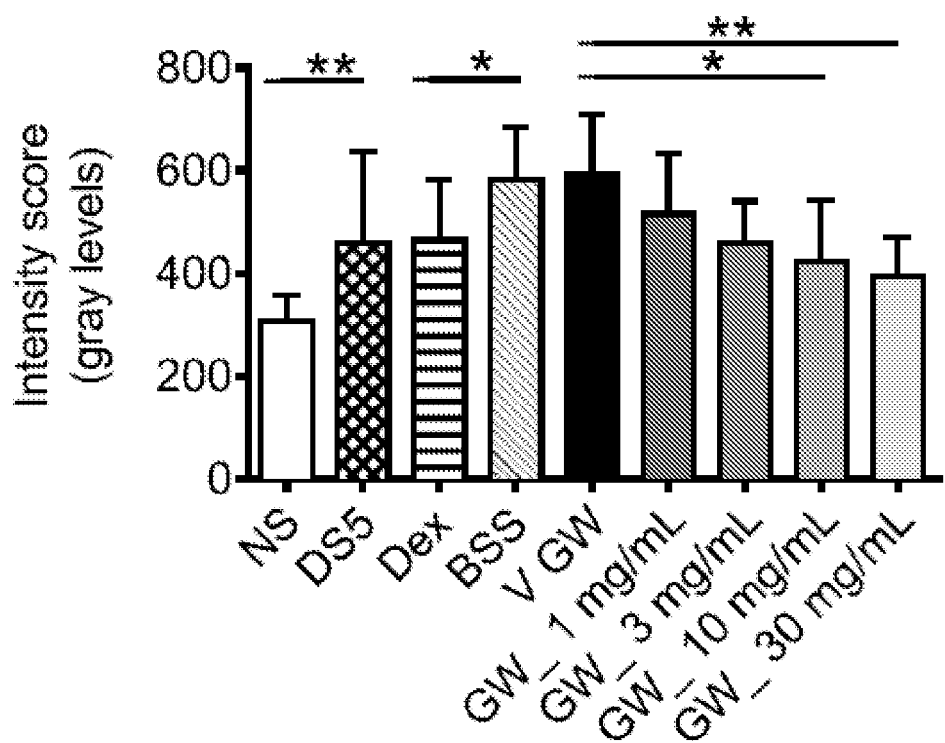
FIG. 1: shows that topical treatment with the compound of formula I dose-dependently prevents DS-induced corneal barrier disruption.

Over 5 days in a controlled DS environment (as described below under Materials and Methods) mice developed corneal barrier dysfunction, evident as punctate corneal OGD staining (as described below under Materials and Methods), as had been reported previously (de Paiva et al., 2009a; de Paiva et al., 2006b). In this murine model, topical administration of the compound of formula I dose-dependently reduced corneal OGD staining similar to a topical corticosteroid, dexamethasone phosphate (FIG. 1). Topical steroids are effective medications for DED if lubricants and non-steroidal immunomodulators are not effective, but they are typically used short-term because of the potential to develop steroid-related ocular adverse events. A similar improvement of corneal staining in this animal model with a different integrin α4β1 antagonist, BIO-8809, had been previously reported (Ecoiffier et al., 2008). Relative to body weight, topical application of a drug to the mouse eye far exceeds the dose given to a human by 2-3 orders of magnitude. It is conceivable that topical treatment in the mouse achieves relevant systemic exposure. Since integrins play a role in leukocyte trafficking it can be reasoned that systemic exposure may be the prerequisite for an integrin antagonist to treat ocular disease. Thus, it was important to determine whether systemic treatment was more effective. Interestingly, when comparing systemic with topical treatment of the same dose side-by-side the compound of formula I improved corneal staining significantly only when administered topically (FIG. 2). This surprising finding suggests that there is a critically important local component to therapy in this disease using the compound of formula I which is required for therapeutic success.

It has been suggested that DED is the consequence of an immune cycle that involves the migration of antigen-presenting dendritic cells (often referred to as APC or DC) from the ocular surface to the draining cervical lymph nodes (CLN) where the priming of autoreactive T cells takes place (Pflugfelder et al., 2008). These autoreactive CD4+ T cells then home back to the ocular surface propagating the disease (Coursey et al., 2013; Niederkorn et al., 2006; Zhang et al., 2012). With integrin receptors present on CD4+ T cells the question arose whether treatment with an integrin α4 antagonist affected T cells in the draining lymph nodes. One day of DS neither increased CD4+ or CD8+ T cells in draining lymph nodes, nor did treatment with the compound of formula I or dexamethasone decrease the number of T cells. As previously reported, 1 day of DS significantly elevated CD11b+ monocytes in draining lymph nodes (Schaumburg et al., 2011; Zhang et al., 2014). But neither of the drug treatments was able to reduce the number of monocytes.

It has been previously shown that DC are important for the immune mediated pathology induced by DS, as DC-depleted mice do not develop DED (Schaumburg et al., 2011). CD11c+ DC appeared elevated in draining lymph nodes, albeit not significantly, by short-term DS. In contrast to topical dexamethasone or systemic treatment with the compound of formula I, which had no significant effect on these cells, activated (MHC-II+) and non-activated CD11c+ cells were decreased by topical treatment with the compound of formula I (FIG. 4). This surprising finding suggests that the compound of formula I prevents the migration of antigen-presenting cells to the draining lymph nodes and that this effect requires drug present at the ocular surface. Similarly, as discussed earlier only topical treatment with the compound of formula I improved corneal staining. Taken together, but without being bound by any particular theory, these results implicate that the compound of formula I acts locally at the level of the ocular surface to treat ocular inflammation related to DED by preventing the migration of antigen-presenting DC to the draining CLN, thus interrupting the immune cycle.

The pro-inflammatory milieu at the ocular surface in DED and this murine model is well described in the literature (Corrales et al., 2006; Coursey et al., 2014; de Paiva et al., 2009a; de Paiva et al., 2006a; de Paiva et al., 2009b; de Paiva et al., 2011). The expression of many cytokines and chemokines is increased in the cornea and conjunctiva resulting in elevated levels in the tear film. In the Examples presented herein, topical treatment with the compound of formula I inhibited the expression of IL-1α, MMP-9, CXCL-9 and TGFβ1 in the corneal epithelium, and of TGFβ1 in the conjunctiva (FIG. 3). IL-1α is a pro-inflammatory cytokine that is released by epithelium and inflammatory cells. Its potential relevance for the disease is highlighted by the clinical development of an IL-1 receptor antagonist for ocular surface inflammation, EBI-005 (Hou et al., 2013; Goldstein et al., 2015). MMP-9 is a protease that has been implicated in the breakage of tight junctions of corneal epithelium and in the corneal barrier disruption in DS (de Paiva et al., 2006b; Luo et al., 2004; Pflugfelder et al., 2005). Tear levels of MMP-9 have been shown to correlate with corneal staining intensity and other clinical parameters in dry eye patients (Chotikavanich et al., 2009). CXCL9, together with CXCL10 and CXCL11, attract interferon-gamma producing Th1 cells and are elevated in the tear film and conjunctiva in dry eye patients (Yoon et al., 2010). TGF-β1 is involved in Th-17 priming together with IL-6 and IL-23 and it is found elevated in tears of dry eye patients (Gutcher et al., 2011; Stockinger et al., 2007; Zheng et al., 2010). Thus, treatment with the compound of formula I reduces some inflammatory markers in this animal model that are associated with ocular surface inflammation in DED.

The Examples demonstrate an improvement in objective signs of dry eye by use of the compound of formula I in the murine DS model. The potent integrin α4 antagonist acted locally at the level of the ocular surface preventing the migration of antigen-presenting cells to the draining lymph nodes with a resulting interruption of the immune cycle of dry eye. Treatment of this disease by blockade of antigen-presenting cell migration represents a novel and previously unknown mechanism of action for integrin antagonists.

II. Methods of Treatment

The term "treatment" or "treating", with respect to treatment of ocular inflammatory conditions, including DED, refers to, inter alia, preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis, and/or preventing disease in a subject who is free there from as well as slowing or reducing progression of existing disease. For a given subject, improvement in a symptom, its worsening, regression, or progression can be determined by an objective or subjective measure. Prophylactic methods (e.g., preventing or reducing the incidence of relapse) are also considered treatment.

In any subject, an assessment may be made as to whether the subject has, or is at risk of having, an ocular inflammatory condition. For example, fluorescein staining of the cornea is used to diagnose dry eye disease. The assessment may indicate an appropriate course of therapy, such as preventative therapy, maintenance therapy, or modulative therapy.

Accordingly, provided herein is a method of treating, preventing, modulating, or attenuating an ocular inflammatory condition by administering to the subject a therapeutically effective amount of a therapeutic agent. The therapeutic agent is a compound of formula I or a pharmaceutically acceptable salt, ester, hydrate, solvate, polymorph, optical isomer, racemate, diastereoisomer or enantiomer thereof. In certain embodiments, the subject is a mammal, such as a human or other mammal.

In certain embodiments, the administration is ocular, such as topical administration or other ocular administration (e.g., local injection). In certain embodiments, the therapeutic agent is delivered to the ocular surface. In certain embodiments, the therapeutic agent is administered topically, e.g., to the cornea, conjunctiva, and/or the eyelid. In certain embodiments, the therapeutic agent is administered topically to the cornea. In certain embodiments, the therapeutic agent is applied to the conjunctival sac or to the eyelid. In certain embodiments, the topical administration involves application of eye drops, ointments, or lotions. In certain embodiments, the therapeutic agent is applied subconjunctivally, intracamerally, intravitreally, subtenon, subretinally, subchoroidally, or suprachoroidally. In certain embodiments, the therapeutic agent is delivered via local injection, such as, for example, periocular, intraocular, subconjunctival, retrobulbar, or intracameral injection. While systemic administration is not preferred, in certain embodiments, the administration may be systemic.

In certain embodiments, administration is achieved by insertion of a sustained release device, such as a mini- or micropump, that releases a therapeutic agent. The sustained release device may be bio-degradable or non-bio-degradable.

A therapeutic agent may be delivered in a pharmaceutically acceptable ophthalmic vehicle, such that the therapeutic agent is maintained in contact with the ocular surface for a sufficient time period to allow the therapeutic agent to penetrate the corneal and internal regions of the eye. The pharmaceutically acceptable ophthalmic vehicle may, for example, be an ointment, vegetable oil or an encapsulating material.

In certain embodiments, the therapeutic agent acts locally to interrupt an immune cycle involving migration of antigen-presenting cells from an ocular surface to a draining lymph node. In certain particular embodiments, the therapeutic agent acts locally to block migration of antigen-presenting cells to a draining lymph node. In certain embodiments, the draining lymph node is a cervical lymph node.

In certain embodiments, the ocular inflammatory condition is dry eye disease, non-infectious uveitis (including anterior, intermediate, posterior, and pan uveitis), non-infectious conjunctivitis, iritis, or scleritis In certain embodiments where the ocular inflammatory condition is dry eye disease, the dry eye disease is caused by, or associated with, allergies, diabetes, lacrimal gland deficiency, systemic lupus erythematosus, graft versus host disease, Parkinson's disease, Sjögren's syndrome, rheumatoid arthritis, complications arising from LASIK therapy for vision correction, contact lens use, exposure to arid climates, air pollution, or cigarette smoke, corneal injury, conjunctival fibrosis, Stevens-Johnson syndrome, congenital alachrima, ocular cictricial pemphigoid, sarcoidosis, or treatment with other drugs that cause symptoms of dry eye disease. In certain embodiments, the ocular inflammatory condition is dry eye disease associated with Sjögren's syndrome. Thus, in one embodiment, the methods comprise administering the therapeutic agent to a human having allergies, diabetes, lacrimal gland deficiency, systemic lupus erythematosus, graft versus host disease, Parkinson's disease, Sjögren's syndrome, rheumatoid arthritis, complications arising from LASIK therapy for vision correction, contact lens use, exposure to arid climates, air pollution, or cigarette smoke, corneal injury, conjunctival fibrosis, Stevens-Johnson syndrome, congenital alachrima, ocular cictricial pemphigoid, sarcoidosis, or who has been treated with other drugs that cause symptoms of dry eye disease.

In general, the dosage of therapeutic agent will vary depending upon such factors as the subject's age, weight, height, gender, general medical condition and previous medical history. Typically, it is desirable to provide the recipient with an individual dose of the therapeutic agent in the range of from about 0.001 mg to about 3000 mg, more particularly about 0.01 mg to about 300 mg, more particularly about 0.1 mg to about 30 mg, more particularly about 0.5 mg to about 10, more particularly about 1 mg to about 5 mg, in each affected eye. In certain embodiments, an individual dose of the therapeutic agent is about 0.6, about 0.8, about 1.0, about 1.2, about 1.4, about 1.6, about 1.8, about 2.0, about 2.2, about 2.4, about 2.6, about 2.8, about 3.0, about 3.2, about 3.4, about 3.6, about 3.8, or about 4.0 mg in each affected eye. In certain embodiments, an individual dose of the therapeutic agent is about 1.8 mg in each affected eye. In certain embodiments, an individual dose of the therapeutic agent is about 3.0 mg in each affected eye. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

For purposes of treatment, including prophylaxis, the therapeutic agent is administered to a subject in a therapeutically effective amount in a pharmaceutically acceptable carrier. A "therapeutically effective amount" is one that is physiologically significant. The therapeutic agent is physiologically significant if its presence results in a detectable change in the physiology of a recipient subject.

In certain embodiments, the pharmaceutical composition contains from about 1 mg/mL to about 100 mg/mL of the therapeutic agent. In certain embodiments, the pharmaceutical composition contains from about 10 mg/mL to about 100 mg/mL of the therapeutic agent. In certain embodiments, the pharmaceutical composition contains from about 10 mg/mL to about 50 mg/mL of the therapeutic agent. In certain embodiments, the pharmaceutical composition contains about 10 mg/mL of the therapeutic agent. In certain embodiments, the pharmaceutical composition contains about 15 mg/mL of the therapeutic agent. In certain embodiments, the pharmaceutical composition contains about 20 mg/mL of the therapeutic agent. In certain embodiments, the pharmaceutical composition contains about 25 mg/mL of the therapeutic agent. In certain embodiments, the pharmaceutical composition contains about 30 mg/mL of the therapeutic agent. In certain embodiments, the pharmaceutical composition contains about 35 mg/mL of the therapeutic agent. In certain embodiments, the pharmaceutical composition contains about 40 mg/mL of the therapeutic agent. In certain embodiments, the pharmaceutical composition contains about 45 mg/mL of the therapeutic agent. In certain embodiments, the pharmaceutical composition contains about 50 mg/mL of the therapeutic agent.

In certain embodiments, the pharmaceutical composition is administered in a volume from about 10 µL to about 100 µL. In certain embodiments, the pharmaceutical composition is administered in a volume from about 20 µL to about 80 µL. In certain embodiments, the pharmaceutical composition is administered in a volume of about 20 µL. In certain embodiments, the pharmaceutical composition is administered in a volume of about 30 µL. In certain embodiments, the pharmaceutical composition is administered in a volume of about 40 µL. In certain embodiments, the pharmaceutical composition is administered in a volume of about 50 µL. In certain embodiments, the pharmaceutical composition is administered in a volume of about 60 µL. In certain embodiments, the pharmaceutical composition is administered in a volume of about 70 µL. In certain embodiments, the pharmaceutical composition is administered in a volume of about 80 µL.

In certain embodiments, the pharmaceutical composition is administered to each affected eye at least once per day. In certain embodiments, the pharmaceutical composition is administered to each affected eye at least twice per day. In certain embodiments, the pharmaceutical composition is administered to each affected eye at least three times per day. In certain embodiments, the pharmaceutical composition is administered to each affected eye at least four times per day. In certain embodiments, the pharmaceutical composition is administered to each affected eye at least five times per day. In certain embodiments, the pharmaceutical composition is administered to each affected eye at least six times per day. In certain embodiments, the pharmaceutical composition is administered to each affected eye at least seven times per day. In certain embodiments, the pharmaceutical composition is administered to each affected eye at least eight times per day. In certain embodiments, the pharmaceutical composition is administered to each affected eye at least nine times per day. In certain embodiments, the pharmaceutical composition is administered to each affected eye at least ten times per day.

In certain embodiments, the therapeutically effective amount is sufficient to achieve a tissue concentration of at least about 240 ng/mL for at least one, at least two, at least three, at least four, at least five, or at least six hour(s) following administration. In certain embodiments, the tissue is a conjunctiva. In certain embodiments, the tissue is cornea. Thus, in certain embodiments, the therapeutically effective amount is sufficient to achieve a conjunctival or corneal tissue concentration of at least about 240 ng/mL for at least one, at least two, at least three, at least four, at least five, or at least six hour(s) following administration. In certain embodiments, the therapeutically effective amount is sufficient to achieve conjunctival or corneal tissue concentrations of at least about 240 ng/mL for at least six hours following administration.

In certain embodiments, the therapeutically effective amount is sufficient to achieve a tissue concentration of at least about 358 ng/mL for at least one, at least two, at least three, at least four, at least five, or at least six hour(s) following administration. In certain embodiments, the tissue is a conjunctiva. In certain embodiments, the tissue is cornea. Thus, in certain embodiments, the therapeutically effective amount is sufficient to achieve a conjunctival or corneal tissue concentration of at least about 358 ng/mL for at least one, at least two, at least three, at least four, at least five, or at least six hour(s) following administration. In certain embodiments, the therapeutically effective amount is sufficient to achieve conjunctival or corneal tissue concentrations of at least about 358 ng/mL for at least six hours following administration.

In certain embodiments, the therapeutically effective amount is sufficient to achieve a tissue concentration of at least about 1000 ng/mL for at least one, at least two, at least three, at least four, at least five, or at least six hour(s) following administration. In certain embodiments, the tissue is a conjunctiva. In certain embodiments, the tissue is cornea. Thus, in certain embodiments, the therapeutically effective amount is sufficient to achieve a conjunctival or corneal tissue concentration of at least about 1000 ng/mL for at least one, at least two, at least three, at least four, at least five, or at least six hour(s) following administration. In certain embodiments, the therapeutically effective amount is sufficient to achieve conjunctival or corneal tissue concentrations of at least about 1000 ng/mL for at least three hours following administration.

In certain embodiments, the therapeutically effective amount administered ocularly results in a biologically insignificant systemic exposure to the therapeutic agent. In certain embodiments, the therapeutically effective amount administered ocularly does not produce systemic immune suppression.

The disclosed therapeutic agents and/or pharmaceutical compositions containing such therapeutic agents may be administered for any suitable period such as at least about 12 weeks, at least about 24 weeks, at least about 36 weeks, or at least about 48 weeks. In certain embodiments, the therapeutic agent is administered for at least 12 consecutive weeks. In certain embodiments, the therapeutic agent is administered for at least 24 consecutive weeks. In certain embodiments, the therapeutic agent is administered for at least 36 consecutive weeks. In certain embodiments, the therapeutic agent is administered for at least 48 consecutive weeks.

In certain embodiments, the treatment comprises daily administration of the therapeutic agent for at least two consecutive weeks. In such a treatment regimen, the therapeutic agent may be administered more than once daily, such as two, three, four, five, six, seven, eight, nine, ten, eleven, or twelve times per day. In certain embodiments, the duration of the treatment regimen exceeds two weeks. In certain embodiments, the duration of the treatment regimen exceeds three weeks. In certain embodiments, the duration of the treatment regimen exceeds four weeks. In certain embodiments, the duration of the treatment regimen exceeds five weeks. In certain embodiments, the duration of the treatment regimen exceeds six weeks. In certain embodiments, the duration of the treatment regimen exceeds seven weeks. In certain embodiments, the duration of the treatment regimen exceeds eight weeks. In certain embodiments, the duration of the treatment regimen exceeds nine weeks. In certain embodiments, the duration of the treatment regimen exceeds ten weeks. In certain embodiments, the duration of the treatment regimen exceeds eleven weeks. In certain embodiments, the duration of the treatment regimen exceeds twelve weeks.

In certain embodiments, the therapeutic agent (e.g., therapeutic agent A) is co-administered with one or more additional therapeutic agents in the same or separate pharmaceutical compositions. Such additional therapeutic agents may include other therapeutic agents used to treat ocular inflammatory conditions.

In certain embodiments, the additional therapeutic agent is cyclosporin A. Cyclosporin A is a cyclic peptide of eleven amino acids, synthesized by a microscopic fungus *Tolypocladium inflatum*. Cyclosporin A has the formula [R—[[R*, R*-(E)]]-cyclic(L-alanyl-D-alanyl-N-methyl-L-leucyl-N-methyl-L-leucyl-N-methyl-L-valyl-3-hydroxy-N,4-dimethyl-L-2-amino-6-octenoyl-L-a-amino-butyryl-N-methylglycyl-N-methyl-L-leucyl-L-valyl-N-methyl-L-leucyl) (CAS number 59865-13-3).

In certain embodiments, the additional therapeutic agent is a steroid. In some such embodiments, the steroid is a glucocorticoid. In some such embodiments, the steroid is difluprednate, prednisolone, dexamethasone, fluocinolone, fluorometholone, loteprednol, medrysone, rimexolone, triamcinolone, cortisone, or hydrocortisone. In certain embodiments, the steroid is dexamethasone (such as dexamethasone base or dexamethasone phosphate), difluprednate, fluocinolone, fluorometholone (such as fluorometholone base or fluorometholone acetate), loteprednol, prednisolone (such as prednisolone acetate or prednisolone phosphate), rimexolone, or triamcinolone (such as triamcinolone acetonide).

In certain embodiments, the additional therapeutic agent is a non-steroidal anti-inflammatory agent. In some such embodiments, the non-steroidal anti-inflammatory agent is selected from the group consisting of bromfenac, diclofenac, flurbiprofen, ketorolac, and nepafenac.

In certain embodiments, the additional therapeutic agent is a LFA antagonist, such as lifitegrast. Lifitegrast is also known as (2S)-2-[[2-(1-benzofuran-6-carbonyl)-5,7-dichloro-3,4-dihydro-1H-isoquinoline-6-carbonyl]amino]-3-(3-methylsulfonylphenyl)propanoic acid and is identified in WO2006/125119, the entire contents of which are herein incorporated by reference.

In certain embodiments, the therapeutic agent can be used in veterinary medicine, particularly in the treatment of ocular inflammatory conditions such as, for example, keratoconjunctivitis sicca in dogs, cats, and horses; chronic superficial keratitis (CSK) in dogs, cats, and horses; and lymphoplasmocytic infiltration of the nictitating membrane in dogs, cats, and horses.

III. Compounds

The compound of formula I can be synthesized using the synthesis described in U.S. Pat. No. 6,867,192, Example 27. The entire contents of U.S. Pat. No. 6,867,192 is hereby incorporated by reference.

Briefly, in one embodiment, 1-(3-dimethylaminopropyl)-3-ethylcarbodiimide hydrochloride (0.4 g) and 1-hydroxybenzotriazole (0.3 g) are added to a solution of (2-methylphenoxy)acetic acid (0.345 g) in acetonitrile (50 ml), under a nitrogen atmosphere. After stirring for 30 minutes at 20° C., 4-[(2S)-2-{[(2S)-2-Amino-4-methylpentanoyl]amino}-3-(tert-butoxy)-3-oxopropyl]phenyl 4-(aminocarbonyl)-1-piperidinecarboxylate hydrochloride (1 g) is added followed by diisopropylethylamine (0.35 ml) and stirring is continued for 18 h. The mixture is concentrated in vacuo and the residue partitioned between 1M hydrochloric acid (100 ml) and ethyl acetate (300 ml). The layers are separated and the organic phase is washed with 1M hydrochloric acid (2×100 ml), saturated aqueous sodium hydrogen carbonate (3×100 ml) and brine (100 ml), dried over magnesium sulphate and evaporated in vacuo to give a white solid. To a solution of this in chloroform (5 ml) is added trifluoroacetic acid (5 ml) and water (1 ml). After stirring for 3 h at 20° C., the solvent is evaporated in vacuo and the residue is azeotroped with toluene (2×20 ml) then triturated with ether to (2S)-3-[4-({[4-(Aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid.

Alternatively, in another embodiment, a solution of (2S)-3-[4-(allyloxy)phenyl]-2-[(tert-butoxycarbonyl)amino]propanoic acid (115.8 g) and 1-hydroxybenzotriazole (48.6 g) in DMF (475 ml) is added to Wang resin (50 g). After 15 minutes 1,3-diisopropylcarbodiimide (56.5 ml) is added and the mixture is stirred for 24 h at 45° C. The resin is filtered and washed with DMF (3×360 ml), methanol (3×360 ml) and dichloromethane (3×700 ml). To a slurry of the resin in dichloromethane (644 ml) is added pyridine (14.7 ml). Acetic anhydride (26.9 ml) is added and the mixture is stirred for 12 h at 20° C. The resin is filtered and washed with dichloromethane (3×550 ml), methanol (3×370 ml) and dichloromethane (3×550 ml).

A slurry of 20 g of the resin in dichloromethane (100 ml) was cooled to 2-5° C. and treated with a solution of phenol (20 g) in dichloromethane (80 ml). Chlorotrimethylsilane (20 ml) is added dropwise and the mixture is stirred for 6 h at 2-5° C. The resin is filtered and washed with dichloromethane (3×200 ml), methanol (3×200 ml), 10% water in DMF (2×200 ml), 10% diisopropylethylamine in DMF (3×200 ml), DMF (200 ml), methanol (3×200 ml) and dichloromethane (3×200 ml).

A slurry of the resin in DMF (55 ml) is treated with a solution of Fmoc-leucine (32.7 g) and 1-hydroxybenzotriazole (12.5 g) in DMF (85 ml). After 5 minutes 1,3-diisopropylcarbodiimide (19.3 ml) is added and the mixture is stirred for 15 h at 20° C. The resin is filtered and washed with DMF (3×150 ml), methanol (3×150 ml) and dichloromethane (3×150 ml).

The resin is treated with 20% piperidine in DMF (180 ml) and stirred for 1 h at 20° C. The resin is filtered and washed with DMF (3×150 ml), dichloromethane (3×150 ml), DMF (3×150 ml) and dichloromethane (3×150 ml). To a slurry of this in DMF (50 ml) is added a solution of (2-methylphenoxy)acetic acid (17.9 g) and 1-hydroxybenzotriazole (14.6 g) in DMF (100 ml). After 5 minutes 1,3-diisopropylcarbodiimide (16.9 ml) is added and the mixture is stirred for 65 h at 20° C. The resin is filtered and washed with DMF (2×150 ml), methanol (3×150 ml) and dichloromethane (3×150 ml).

A slurry of the resin in dichloromethane (60 ml) is treated with a solution of tetrakis(triphenylphosphine)palladium(0) (5.21 g) in dichloromethane (140 ml) followed by morpholine (13 ml). The mixture is stirred for 2 h at 20° C. then the resin is filtered and washed with dichloromethane (7×200 ml).

A slurry of the resin in dichloromethane (160 ml) is treated with diisopropylethylamine (12.4 ml) followed by 4-nitrophenyl chloroformate (24.8 g) in 3 portions at 5 minute intervals. The mixture is stirred for 1 h at 20° C. The resin is filtered and washed with dichloromethane (3×200 ml). The resin is treated with a solution of isonipecotamide (15.8 g) in DMF (180 ml) and the mixture is stirred for 1.5 h at 20° C. The resin is filtered and washed with DMF (4×200 ml) and dichloromethane (2×200 ml).

The resin is treated with 50% TFA in dichloromethane (200 ml). After stirring for 1 h at 20° C. the resin is filtered and washed with dichloromethane (5×200 ml). The combined filtrate and washings were evaporated in vacuo. The residue is azeotroped with toluene (2×100 ml) then triturated with ether (50 ml) and the resulting white solid filtered. To this is added acetonitrile (150 ml) and the mixture is heated to reflux. The resulting suspension is allowed to cool to 20° C. and stirred for 18 h. The mixture is filtered to give (2S)-3-[4-({[4-(Aminocarbonyl)-1-piperidinyl]carbonyl}oxo)phenyl]-2-[((2S)-4-methyl-2-{[2-(2-methylphenoxy)acetyl]amino}pentanoyl)amino]propanoic acid.

In certain embodiments, the therapeutic agent (e.g., therapeutic agent A) is a pharmaceutically acceptable salt of compound (I). The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In certain embodiments, the therapeutic agent (e.g., therapeutic agent A) is a potassium salt of compound (I).

In certain embodiments, the compound of formula (I) is administered as a conjugate, complex, or prodrug. In certain embodiments, the compound of formula (I) is administered in the form of a prodrug. Such prodrug may be metabolized by the subject to provide the compound of formula (I).

IV. Pharmaceutical Compositions

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

The composition can be formulated according to known methods to prepare pharmaceutically useful compositions, whereby a compound is mixed with a pharmaceutically acceptable carrier. Sterile phosphate-buffered saline is one example of a pharmaceutically acceptable carrier. Other suitable carriers are well known to those in the art. See, for example, REMINGTON'S PHARMACEUTICAL SCI- ENCES, 19th Ed. (1995). Pharmaceutical compositions adapted for topical administration may be formulated as ointments, creams, emulsions, suspensions, lotions, powders, solutions, pastes, gels, sprays, mists, aerosols or oils. In certain embodiments, the pharmaceutical composition is a solution, such as an ophthalmic solution. In such embodiments, the ophthalmic solution is administered to humans or non-human mammals via the topical route, in the form of one or more drops per day in each eye.

For treatments of the eye the compositions may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Formulations to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The instant compositions may be applied topically to the eye, subconjunctivally, intracamerally, intravitreally, sub-tenon, subretinally, subchoroidally, suprachoroidally, in the conjunctival sac or to the eyelid using an ocular delivery device or insert. Such a device or insert may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Formulations for drug delivery using ocular devices or inserts may combine one or more active agents and adjuvants appropriate for the indicated route of administration. For example, the active agents may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers, and a carrier or diluent that has a time delay property. Representative examples of biodegradable compositions can include albumin, gelatin, starch, cellulose, dextrans, polysaccharides, poly (D,L-lactide), poly (D,L-lactide-co-glycolide), poly (glycolide), poly (hydroxybutyrate), poly (alkylcarbonate) and poly (orthoesters) and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005), herein incorporated by reference for purposes of its teachings of examples of polymers for use in ocular drug delivery.

V. Kits

Also provided herein are kits, e.g., kits for therapeutic purposes. A kit may comprise one or more compounds as described herein, e.g., in premeasured doses. A kit may optionally comprise devices for contacting cells with the compounds and instructions for use.

Devices include syringes, implantable pumps, such as mini- and micropumps, and other devices for ophthalmic use.

Also provided herein are therapeutic combinations comprising therapeutic agent A and another therapeutic agent (the same ones used in combination therapies and combination compositions) in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The compound and the other agent are preferably packaged together in a blister pack or other multi-chamber package, or as connected, separately sealed containers (such as foil pouches or the like) that can be separated by the user (e.g., by tearing on score lines between the two containers).

In still another embodiment, the invention provides a kit comprising in separate vessels, a) a compound of this invention; and b) another therapeutic agent such as those described elsewhere in the specification.

EXAMPLES

Materials

[3H] GW559090 was custom synthesized at Amersham to contain five 3H atoms per molecule giving a specific activity of 76 Ci/mmol.

All animal studies were conducted using C57BL/6 mice, 6 to 8 weeks old, which were purchased from Jackson Labs (Bar Harbor, Me.).

Binding and Cell Adhesion

Jurkat J6 cells (human lymphoblast cell line) were grown as a suspension culture in RPMI 1640 supplemented with FCS (10%) and glutamine (2 mM). RPMI8866 cells (human B lymphoid cell line) were grown as a suspension culture in RPMI 1640 supplemented with FCS (10%) and glutamine (2 mM). RBL-2H3 cells (rat basophilic cell line) were cultured in Eagle's MEM plus Earles salts supplemented with 2 mM L-glutamine, 1 mM sodium pyruvate, 1× non-essential amino acids, 1 mM Na pyruvate 10% heat inactivated foetal calf serum.

J6 Saturation Assay (Filtration Assay):

Binding of the compound of formula I was characterized in human J6 cells which express VLA-4. J6 cells were harvested by centrifugation for 5 minutes at 500 g and resuspended in assay buffer (50 mM HEPES, pH 7.5, 100 mM NaCl, 2 mM glucose, 1 mM MnCl2). Each well contained $1\times10^6$ cells and either 10 µM cold GW559090, to define the NSBs (non-specific binding), or buffer. [3H] GW559090 (0.02-50 nM) was added in a final volume of 500 µL and incubated for 2 h at 37° C. Bound [3H] GW559090 was separated from free by rapid vacuum filtration through pre-soaked Whatman GF/B filters, followed by three washes in ice-cold buffer, scintillant was then added to filter discs and disintegrations per minute measured on a Beckman Scintillation counter. The actual amount of [3H] GW559090 added for each concentration of the saturation curve was measured by counting disintegrations from a 50 µL aliquot of the label dilution range.

Saturation Binding Assay in RBL-2H3 Cells (SPA Assay):

The assay buffer contained 50 mM HEPES, 100 mM NaCl, 1 mM MnCl2, pH 7.5 (with NaOH). WGA SPA beads were used at 1 mg/well. Cells were harvested and resuspended in assay buffer and 1 million cells were added per well in a white bottomed plate. Cold GW559090 to give a final assay concentration of 20 µM (to define nonspecific binding) or buffer alone were added and then [3H] GW559090 across a concentration range across the plate was added (nominal [3H] GW559090 concentration range was 0.01 to 200 nM). The final assay volume was 250 µL. The plate was then incubated at 37° C. for 2 h. Disintegrations were counted by scintillation (from the WGA SPA beads) in a Wallac Microbeta plate reader.

The actual amount of [3H] GW559090 added for each concentration of the saturation curve was measured by counting disintegrations per minute from a 50 µL aliquot of the label dilution range.

VCAM Cell Adhesion Assay:

Polystyrene 96-well microtitre plates were coated with IgG at a concentration of 0.05 mg/mL in bicarbonate buffer for 2 hours at 37° C. The solution was aspirated and the plates washed twice with PBS. The plates were then incubated overnight at 4° C. with a 1:4000 dilution of VCAM-1 of 3% BSA in PBS. Prior to use the VCAM-1 was aspirated and the plates washed twice with PBS.

J6 or RPMI cells (as required) were labelled with the fluorescent dye BCECF-AM (10 µM and $6\times10^6$ cells/mL) for 10 min at 37° C. before the excess was removed by centrifugation at 500 g for 5 min and the cells resuspended at a cell concentration of $1.2\times10^7$ cells/mL in HBSS. Equal volumes HBSS containing the compound of formula I (over concentration range 38.1 pM to 10 µM) and cells were added to the VCAM-1 coated plates. After a 30 minute incubation at 37° C., non or loosely adhering cells were removed by inverting the plate and blotting on tissue paper. Two washes with PBS and blotting were followed by addition of Triton X-100 (2% v/v). The plates were counted in a Wallac Viktor. Compounds that inhibited adhesion resulted in a lower fluorescence reading.

MAdCAM Cell Adhesion Assay:

Polystyrene 96-well microtitre plates were coated with IgG at a concentration of 0.05 mg/mL in bicarbonate buffer for 2.5 hours at 37° C. The solution was aspirated and the plates washed twice with PBS. The plates were then incubated overnight at 4° C. with MAdCAM at a concentration of 204.0 ng/mL in 3% BSA in PBS. Prior to use the MAdCAM was aspirated and the plates washed twice with PBS. J6 or RPMI cells (as required) were labelled with the fluorescent dye BCECF-AM (10 µM and $6\times10^6$ cells/mL) for 10 min at 37° C. before the excess was removed by centrifugation at 500 g for 5 min and the cells resuspended at a cell concentration of $1.2\times10^7$ cells/mL in HBSS. Equal volumes of HBSS containing the compound of formula I (over concentration range 38.1 pM to 10 µM) and cells were added to the MAdCAM coated plates. Adhesion took place over a 30-minute incubation at 37° C. Non or loosely adhering cells were removed by inverting the plate and blotting on tissue paper. Two washes with PBS and blotting were followed by addition of Triton X-100 (2% v/v). The plates were counted in a Wallac Viktor.

CS-1 Cell Adhesion Assay:

Polystyrene 96-well microtitre plates were coated with CS-1 (connecting segment 1, a cell attachment domain of fibronectin) at a concentration of 0.01 mg/mL in bicarbonate buffer overnight at 4° C. The solution was aspirated and the plates washed twice with PBS. The plates were then incubated at room temperature in the presence of 3% BSA for 60 min, 'flicked' to expel the BSA and washed twice in bicarbonate buffer. J6 or RPMI cells (as required) were labelled with the fluorescent dye BCECF-AM (10 µM and $6\times10^6$ cells/mL) for 10 min at 37° C. before the excess was removed by centrifugation at 500 g for 5 min and the cells resuspended at a cell concentration of $1.2\times10^7$ cells/mL in HBSS. Equal volumes of HBSS containing the compound of formula I (over concentration range 19.0 pM to 5 µM) and cells were added to the CS-1 coated plates. Adhesion took place over a 30 minute incubation at 37° C. Non or loosely adhering cells were removed by inverting the plate and blotting on tissue paper. Two washes with PBS and blotting were followed by addition of Triton X-100 (2% v/v). The plates were counted in a Wallac Viktor.

Induction of Desiccating Stress, Treatment Regimen

Female C57BL/6 mice, aged 6 to 8 weeks, were subjected to DS for 5 days (DS5) as described previously (de Paiva et al., 2006b; Niederkorn et al., 2006). Topical bilateral treatment with 1 eye drop per eye (2 µL volume) or subcutaneous injection (4 µL volume), 2 times per day, was initiated on day 1 concurrently with DS and continued through day 4. Treatment with the compound of formula I or dexamethasone phosphate 0.1% was compared to correspondingly treated vehicle controls. Mice were randomized to receive one of the test articles. Control mice were kept in a non-stressed (NS) environment maintained at 50-75% relative humidity without exposure to airflow or scopolamine and were not treated with test or control article. Treatment effects were assessed on corneal staining with Oregon Green Dextran (OGD); expression of inflammatory markers in ocular surface tissues by real time PCR; cell population analysis in draining cervical lymph nodes by FACS analysis; conjunctival T cell infiltration by immunohistochemistry.

Corneal OGD Staining

On the morning of the 5th day, mice received one s.c. dose of scopolamine. Two hours later corneal staining was assessed using Oregon Green Dextran (OGD-488), which is a conjugated fluorescent dye of a 70 kDa molecular size (Invitrogen-Molecular Probes) as previously described (de Paiva et al., 2006b). The procedure consisted of instillation of 0.5 μL of OGD on the cornea using a glass capillary pipette, 1 minute before euthanasia. Mice were euthanized by inhalation of isoflurane gas followed by cervical dislocation. Eyes were then rinsed with 2 mL of BSS. Excess liquid was carefully blotted from the ocular surface with filter papers without touching the cornea. Digital pictures of both eyes were taken under 470 nm excitation and 488 nm emission wave lengths using a Nikon SMZ-1500 stereo microscope, with an exposure time of 2 seconds. Both eyes from each animal were evaluated; the right eye always first followed by the left eye. The mean intensity in the central cornea was evaluated from digital images using NIS Elements (version 3.0) by placing a fixed region of interest (a 2-mm diameter circle) on the central cornea. The mean intensity of the fluorescence was read by the software and stored in a database (Excel, Microsoft). This fluorescence measurement in the central ring was done independently by 2 masked observers, for each mouse eye. By the conclusion of the experiment, results were averaged from both observers using all data collected during all study weeks (Excel, Microsoft). Results are presented as geometric mean±95% confidence interval of gray levels.

RNA Isolation and Reverse Transcription

Total RNA was isolated from corneal and conjunctival epithelia that was collected and pooled from 2 eyes (right and left) at each time point from untreated control mice, mice subjected to DS for 5 days (DS5), DS5 mice topically treated with the compound of formula I (30 m/mL) and vehicle treated animals (n=7/group) using a PicoPure™ RNA Isolation Kit (Acturus Bioscience Inc, Mountain View, Calif., USA) following the manufacturer's protocol. Briefly, corneal epithelial cells were scraped and whole conjunctiva was cut and placed in 100 μL of extraction buffer and incubated at 42° C. for 30 minutes. The cell extract was loaded onto a preconditioned purified column, which was centrifuged, treated with DNase (Qiagen, Valencia, Calif., USA) and washed twice with two different wash buffers. The RNA was eluded in 12 μL of low ionic strength buffer. The RNA concentration was measured by absorption at 260 nm using a spectrophotometer (NanoDrop 2000, Thermo Scientific, Wilmington, Del., USA) and samples were stored at −80° C. until use. First-strand cDNA was synthesized from 1 μg of total RNA with random hexamers using M-MuLV reverse transcriptase (Ready-To-Go You-Prime First-Strand Beads; Amersham Pharmacia Biotech, Inc., Piscataway, N.J.) as previously described (de Paiva et al., 2006a).

Absolute Real Time Polymerase Chain Reaction

A cDNA aliquot (1-4 μL) from samples was used for real time PCR in a total volume of 10 μL containing the following per reaction: 0.3 μL of gene specific Taqman probes used and 5 μL of 2× Taqman Fast PCR Master Mix, (Applied Biosystems). Real time PCR was performed on a StepOnePlus™ Real-Time PCR System (Applied Biosystems) and the parameters consisted of pre-denaturation at 95° C. for 22 sec, followed by 40 cycles of denaturation at 95° C. for 1 sec, annealing and extension at 60° C. for 20 sec. Samples and standards were assayed in duplicate. A non-template control and total RNA without retrotranscription were included in all the experiments to evaluate PCR and DNA contamination of the reagents used. The following mouse Taqman probes were used: IL-1α (Mm00439620); MMP-9 (Mm00442991); CXCL9 (Mm004434946); TGF-β1 (Mm00441724) and HPRT-1 (Mm00446968). The HPRT-1 gene was used as an endogenous reference for each reaction. The results of quantitative PCR were analyzed by the comparative $C_T$ method where target change=2-ΔΔ $C_T$. The results were normalized by the $C_T$ value of HPRT-1 of the untreated control group (de Paiva et al., 2006b).

Dissection of Draining Lymph Nodes

Cervical draining lymph nodes (CLN) were surgically excised, placed in a round culture plate with ~8 mL of complete RPMI media and smashed between two frosted slides.

Flow Cytometry

Single-cell suspensions of CLN from C57BL/6 mice, treated under DS conditions for 1 day, were prepared, centrifuged and sequentially filtered, as previously described (de Paiva et al., 2009a). Subsequently 1.0 mL of ACT solution was added for 30 seconds followed by 2.0 mL of complete RPMI. The cells were once again centrifuged and the supernatant aspirated. Cells were then re-suspended in 2.0 mL of complete RPMI and prepared for counting. Ten μL of Trypan Blue were used for counting and the cells were divided in tubes at 1×10$^6$ cells/mL. Subsequently, the cells were incubated on ice in 20 μL unconjugated anti-mouse CD16/CD32 (BD Pharmingen, San Diego, Calif.) followed by 80 μL of directly conjugated primary antibody or isotype. Finally the samples were washed with 1 mL PBS/1% FBS, centrifuged and re-suspend in 0.3 mL PBS/1% FBS containing 1:1000 of PI. The samples were stored at 4° C. until the analysis was performed with an A BD LSRII Benchtop cytometer. The data was analysed using BD Diva Software (BD Pharmingen) and FlowJo (TreeStar Inc).

Conjunctival T Cell Infiltration

For immunohistochemistry, the eyes and adnexa of 5 mice/group (n=5) were excised, embedded in optimal cutting temperature (OCT compound; VWR, Suwanee, Ga.), and flash frozen in liquid nitrogen. Sagittal 8-μm sections were cut with a cryostat (HM 500; Micron, Waldorf, Germany) and placed on glass slides that were stored at −80° C. Immunohistochemistry was performed to detect and count the cells in the conjunctival epithelium and stroma that stained positively for CD4 (clone H129.9, 10 μg/mL, BD Bioscience, San Diego, Calif.). Cryosections were stained with the above mentioned primary antibody and appropriate biotinylated secondary antibody (BD Pharmingen) and Vectastain Elite ABC using NovaRed reagents (Vector, Burlingame, Calif.). Secondary antibody alone and appropriate anti-mouse isotype (BD Biosciences) were also used as controls. Two sections from each animal were examined and photographed with a microscope equipped with a digital camera (Eclipse E400 with a DS-Fi1; Nikon). Positively stained cells were counted in the goblet cell rich area of the conjunctiva, over a length of at least 500 μm in the epithelium for a distance of 500 μm using image-analysis software (NIS Elements Software, version 3.0, BR, Nikon).

Statistical Analysis

Due to skewed distribution of OGD data, the analysis was done on the log 10 scale to make the data more normally distributed. Log 10 OGD data was averaged across two observers and the left and right eyes. The mixed effects ANOVA model included treatment group as a fixed effect and week as a random effect. 95% and 99% confidence intervals were constructed for the disease (5 day DS vs untreated group kept in separate vivarium) and compound treatment effects (treatment vs vehicle). As these comparisons were all pre-planned (comparing each treatment to its vehicle group), no adjustment was made for multiplicity. Log 10 scale treatment effect estimates and confidence limits were converted back to the original OGD scale, thus representing the estimate for the ratio of group geometric means and their confidence limits. For gene expression analysis, an unpaired T test was performed to compare drug and vehicle treatment. For flow cytometry analysis, a 2-way ANOVA with fixed treatment and random experiment effects was employed to test the treatment differences. The analysis was followed by Dunnett's multiple comparison procedure to compare each of the treatment groups with the vehicle group. T cell density was calculated for each section and averaged across sections for each animal. As the distribution of average cell density data was non-normal, it was analyzed by using non-parametric methods (Kruskal-Wallis procedure, followed by Dunn's multiple comparisons technique).

Example 1. Pharmacology of GW559090

[3H]GW559090 binding to human J6 cells was saturable and was described in these experiments by a single binding site with mean Kd of 0.19 nM (0.08-0.43) (geometric mean and 95% CL) derived from 4 separate experiments. A single high affinity binding site for [3H] GW559090 was also shown in rat RBL-2H3 cells which express rat $\alpha 4\beta 1$, mean Kd 1.04 nM (0.58-1.89).

Inhibition of cell adhesion was determined for $\alpha 4\beta 1$ (Jurkat J6 cells) to VCAM-1 and CS-1 (fibronectin domain); for $\alpha 4\beta 7$ (RPMI 8866 cells) to MAdCAM in coated microtiter plates. GW559090 inhibited J6 cell adhesion to VCAM-1 in a monophasic fashion with a mean IC50 of 7.72 nM (2.39-24.9). GW559090 also inhibited J6 cell adhesion to CS-1 with a mean IC50 of 8.04 nM (3.05-21.2) and to MAdCAM in a biphasic manner, supporting the presence of a high and low affinity site for MAdCAM-GW559090 binding in J6 cells. The RPMI 8866 MAdCAM binding predominantly measures $\alpha 4\beta 7$ mediated cell adhesion. GW559090 inhibited RPMI 8866 cell adhesion to MAdCAM with an IC50 of 23.0 nM (20.0-26.4). GW559090 also inhibited RPMI 8866 binding to VCAM-1, and CS-1 in a simple monophasic manner with respective IC50s of 4.81 nM (2.82-8.20) and 24.5 nM (identical duplicate values).

TABLE 1

Binding of [3H] GW559090 to $\alpha 4$ integrins and inhibition of cell adhesion

| Binding (Kd) | Human $\alpha 4\beta 1$ | 0.19 nM |
|---|---|---|
| | Rat $\alpha 4\beta 1$ | 1.04 nM |
| Inhibition of cell adhesion (IC50) | $\alpha 4\beta 1$-VCAM-1 | 7.72 nM |
| | $\alpha 4\beta 1$-CS-1 | 8.04 nM |
| | $\alpha 4\beta 7$-MAdCAM | 23.0 nM |

Additionally, the compound of formula I had been reported as highly selective vs. non-$\alpha 4$ integrins, including LFA-1 (Ravensberg et al., 2006). No significant inhibition was observed by the compound of formula I (at 10 µM) in radioligand binding assays on 53 receptors and 4 transporters in an MDS Pharma screen.

Example 2. Topical Treatment with the Compound of Formula I Prevents Desiccation-Induced Corneal Barrier Disruption We found a significant increase in corneal permeability measured by OGD staining between the untreated nonstressed (NS) and dry eye control groups (DS5, FIG. 1). Because corticosteroid therapy has been reported to improve corneal epithelial disease of dry eye both in humans and mice (de Paiva et al., 2006a; de Paiva et al., 2006b; Marsh and Pflugfelder, 1999), we used topical treatment with Dexamethasone (Dex) as positive control. Treatment with 0.1% Dex significantly improved OGD intensity scores. A range of doses of the compound of formula I, as low as 1 mg/mL and as high as 30 mg/mL, was investigated. A significant decrease in OGD intensity scores was noted with increasing concentrations of the compound of formula I vs. its vehicle. The most efficacious concentration was 30 mg/mL (FIG. 1) which was therefore used in subsequent studies.

Example 3. The Compound of Formula I Acts Topically on the Ocular Surface

To explore the effect of systemic administration of the compound of formula I on corneal staining, two routes of administration, topical and subcutaneous (SC), were compared. An identical dose was given SC (120 µg as one 4 µL bolus) and topically (60 µg as a 2 µL drop to each eye). Mice receiving the compound of formula I systemically were also given vehicle eye drops topically. As shown in FIG. 2, and similar to FIG. 1, topical dexamethasone decreased OGD uptake. Topical treatment with the compound of formula I again significantly decreased DS-induced corneal barrier disruption compared to its vehicle. This effect was not observed when the compound of formula I was administered systemically. These results indicate that the local therapeutic effect of the compound of formula I is achieved by topical administration as traditional eye drops. This represents a surprising finding given the known role of integrins in leukocyte trafficking from the bloodstream which should require systemic drug exposure. This local action from topically administered drug is suggestive of a novel mechanism of action for an $\alpha 4$ integrin antagonist.

Example 4. Topical Treatment with the Compound of Formula I Decreases Inflammatory Markers on the Ocular Surface DED is often accompanied by increased T-cell related cytokines, matrix-metalloproteinases and inflammatory cytokines in cornea and conjunctiva (Coursey et al., 2014; de Paiva et al., 2009a; Yoon et al., 2010). We investigated the expression of IL-1$\alpha$, TGF-$\beta$1, MMP-9 and CXCL-9 in cornea and conjunctiva using mice that were topically treated with the compound of formula I at 30 mg/mL during 5 days of DS and compared to vehicle dosed mice. These genes were chosen since they are highly inducible by DS (Coursey et al., 2014; de Paiva et al., 2009a; de Paiva et al., 2006b; de Paiva et al., 2006a; Yoon et al., 2007). Both experimental groups and non-stressed controls had similar expression of the housekeeping gene; experimental groups were calibrated to non-stressed control. The results are presented in FIG. 3.

There was a significant decrease in IL-1$\alpha$, MMP-9, TGF-$\beta$1 and CXCL9 transcripts in corneas treated with GW559090 compared to vehicle control (FIG. 3A). In conjunctiva, there was a significant reduction in TGF-$\beta$1, expression but no change regarding IL-1$\alpha$, MMP-9 and CXCL-9 (FIG. 3B). These results indicate that the compound of formula I can decrease markers of inflammation at the ocular surface.

Example 5. Topical Treatment with the Compound of Formula I Decreases Dendritic Cell Activation The draining CLN are an integral part of the immune cycle in DED (Pflugfelder et al., 2008; Schaumburg et al., 2011). To determine the impact of the compound of formula I, if any, on the CLN, mice were subjected to DS for 1 day and treated either topically or systemically (subcutaneous; identical 120 μg dose as topical) twice-daily with the compound of formula I. Mice receiving subcutaneous drug were concomitantly administered vehicle topically to both eyes to mimic the wetting of the ocular surface that occurs with a topical eye drop. Draining CLN were excised and prepared for flow cytometry analysis of T cells (CD4, CD8), monocytes (CD11b), dendritic cells (CD11c) and MHC II.

One day of DS led to a significant increase in CD11b$^+$ monocytes in CLN compared to normal mice. None of the other cell populations studied were significantly altered by DS in draining CLN. None of the treatments had an impact on either of the T cell populations or CD11b+ monocytes. While CD11c$^+$ and CD11c$^+$/MHC II$^+$ cells tended to be increased by DS, albeit not significantly, topical treatment with the compound of formula I reduced both, activated and non-activated, forms of DCs compared to the vehicle control group. Neither systemic treatment with the compound of formula I nor topical treatment with dexamethasone phosphate produced the same effect. The results are presented in FIG. 4.

The fact that the compound of formula I inhibited antigen-presenting cell migration to the CLN and improved corneal staining in this murine model of dry eye only when administered topically, but not when administered systemically, is an intriguing finding. It suggests a local rather than systemic effect by the integrin α4 antagonist in the treatment of DED. This local effect appears to be specific to the integrin α4 antagonist GW559090 and differentiated from topical steroid treatment (dexamethasone phosphate) in that topical dexamethasone phosphate ameliorated DED associated corneal staining, but not the migration of antigen-presenting cells to the draining lymph nodes. It can be appreciated by someone skilled in the art from those considerations that the therapeutic effect of integrin α4 antagonism employs a unique and novel mechanism.

Example 6. PK Study in Rabbits

The potassium salt of GW559090, referred to herein as GW559090A, was given to male New Zealand White rabbits by topical ocular administration as a single bilateral drop (Study #1: n=2 rabbits/4 eyes per time point; Study #2: n=3 rabbits/6 eyes per time point). At designated times (0.5, 1, 3, 6 hours post administration), ocular tissues were collected and processed for analysis. Concentrations of GW559090 were measured in cornea and bulbar conjunctiva by liquid chromatography with tandem mass spectrometry (LC-MS/MS).

Following a single topical administration of 40 μL (50 mg/mL), Cmax values in bulbar conjunctiva were observed at 1 hour postdose (Tmax) for both studies. Mean conjunctiva concentrations generally declined over time and were quantifiable through 6 hours postdose. Following a single topical administration of 40 μL (50 mg/mL), mean Cmax values in cornea were observed at 0.5 hours postdose (Tmax) for both studies. Mean cornea concentrations generally declined over time and were quantifiable through 6 hours postdose. Mean cornea concentrations were higher than mean conjunctiva concentrations at the 3 and 6 hour postdose time points. Conjunctival and corneal tissue concentrations of approximately 358 ng/mL persisted up to 6 hours (FIG. 6). The conjunctival and corneal tissue concentrations were in excess of 3000 ng/mL at 30 minutes and levels persisted above 1000 ng/mL in corneal tissue at 3 hours (FIG. 6).

Example 7. Topical Ocular Administration to New Zealand White Rabbits for 13 Weeks GW559090A was Used in this Study. Doses and Concentrations in this Example are Expressed in Terms of the Parent Compound, GW559090

GW559090A was given to New Zealand White Rabbits by topical ocular administration for 13 weeks. Animals were dosed six or twelve times per day, with one hour between doses. Treatment groups were: (1) vehicle (12 times a day), (2) 30 mg/mL/occasion given six times a day, (3) 50 mg/mL/occasion given six times a day, or (4) 50 mg/mL/occasion, given 12 times a day.

GW559090A was formulated as a stock solution in 25 mM phosphate buffer with 0.5% sodium chloride to provide a 50 mg/mL stock solution, which was used for administration to Groups 3 or 4, or further diluted with 25 mM phosphate buffer with 0.75% sodium chloride to provide a 30 mg/mL solution for administration to Group 2. Control animals were treated with the vehicle for 50 mg/mL solution (25 mM phosphate buffer with 0.5% sodium chloride).

During the 13 week treatment period rabbits received daily topical ocular doses of GW559090A or vehicle at a constant dose volume of 0.06 mL (given 6 or 12 times a day, with one hour between doses). The test article formulation or vehicle was carefully dropped into the partially everted lower eyelid of the right eye from a suitable distance, to prevent contact of the positive displacement pipette with the eye. The lower and upper lids were then gently held together for approximately five seconds, to prevent loss of dose and aid even distribution across the external ocular surface. The un-dosed eye was not manipulated at any time and served as a within animal untreated control site.

Instillation of GW559090A for 13 weeks by topical ocular administration at 30 or 50 mg/mL/occasion six times a day or 50 mg/mL/occasion, 12 times a day, with one hour between doses, was well-tolerated and caused no ocular change or systemic toxicity. The No-Observed-Adverse-Effect level (NOAEL) was 50 mg/mL/occasion, 12 times a day, with one hour between doses. At this dose, based on Week 13 values, AUC0-1 (0-24) exposure was 19.6 (235) ng·h/mL for males and 35.5 (426) ng·h/mL for females; Cmax was 38.1 g/mL for males and 68.0 ng/mL for females.

The composite mean toxicokinetic parameters for GW559090 from male and female rabbits following ocular administration of GW559090A are shown in Table 2 and Table 3, respectively.

TABLE 2

Composite Mean Toxicokinetic Parameters for GW559090 from Male Rabbits Following Ocular Administration of GW559090A

| | | Male Dose of GW559090 (mg/mL) | | |
|---|---|---|---|---|
| Parameter | Period | 30$^a$ | 50$^a$ | 50$^b$ |
| AUC$_{0-1}$(AUC$_{0-24}$) (ng · h/mL) | Day 1 | 7.86 (47.2) | 14.4 (86.4) | 12.1 (145) |
| | Week 4 | 9.23 (55.4) | 17.9 (107) | 11.6 (139) |
| | Week 13 | 9.10 (54.6) | 17.6 (106) | NA |
| | Week 14 | NA | NA | 19.6 (235) |
| C$_{max}$$^c$ (ng/mL) | Day 1 | 30.8 | 105 | 66.3 |
| | Week 4 | 51.4 | 80.4 | 41.4 |
| | Week 13 | 11.8 | 32.2 | NA |
| | Week 14 | NA | NA | 38.1 |

TABLE 2-continued

Composite Mean Toxicokinetic Parameters for GW559090 from Male
Rabbits Following Ocular Administration of GW559090A

| Parameter | Period | Male Dose of GW559090 (mg/mL) | | |
|---|---|---|---|---|
| | | $30^a$ | $50^a$ | $50^b$ |
| $T_{max}^c$ (h) | Day 1 | 0.083 | 0.083 | 0.083 |
| | Week 4 | 0.083 | 0.083 | 0.083 |
| | Week 13 | 0.083 | 0.083 | NA |
| | Week 14 | NA | NA | 0.5 | a. 6 daily doses
b. 12 daily doses
c. After the first daily dose
NA: Not Applicable

TABLE 3

Composite Mean Toxicokinetic Parameters for GW559090 from
Female Rabbits Following Ocular Administration of GW559090A

| Parameter | Period | Female Dose of GW559090 (mg/mL) | | |
|---|---|---|---|---|
| | | $30^a$ | $50^a$ | $50^b$ |
| $AUC_{0-1}$ ($AUC_{0-24}$) (ng · h/mL) | Day 1 | 4.19 (25.1) | 11.0 (66.0) | 7.30 (87.6) |
| | Week 4 | 10.6 (63.6) | 12.6 (75.6) | 13.1 (157) |
| | Week 13 | 9.83 (59.0) | 15.7 (94.2) | NA |
| | Week 14 | NA | NA | 35.5 (426) |
| $C_{max}^c$ (ng/mL) | Day 1 | 16.0 | 67.8 | 30.6 |
| | Week 4 | 32.4 | 44.4 | 56.6 |
| | Week 13 | 23.5 | 49.7 | NA |
| | Week 14 | NA | NA | 68.0 |
| $T_{max}^c$ (h) | Day 1 | 0.083 | 0.083 | 0.083 |
| | Week 4 | 0.083 | 0.083 | 0.083 |
| | Week 13 | 0.25 | 0.083 | NA |
| | Week 14 | NA | NA | 0.083 | a. 6 daily doses
b. 12 daily doses
c. After the first daily dose
NA: Not Applicable
"$AUC_{0-24}$" refers to $AUC_{0-1}$ multiplied by total number of daily doses to represent total daily estimated AUC.

Example 8. Topical Ocular Administration to Beagle Dogs for 13 Weeks

GW559090A was used in this study. Doses and concentrations in this Example are expressed in terms of the parent compound, GW559090.

GW559090A was given to Beagle Dogs by topical ocular administration for 13 weeks. Animals were dosed six or twelve times per day, with one hour between doses. Treatment groups were: (1) vehicle (12 times a day), (2) 30 mg/mL/occasion given six times a day, (3) 50 mg/mL/occasion given six times a day, or (4) 50 mg/mL/occasion, given 12 times a day.

GW559090A was formulated as a stock solution in 25 mM phosphate buffer with 0.5% sodium chloride to provide a 50 mg/mL stock solution, which was used for administration to Groups 3 or 4, or further diluted with 25 mM phosphate buffer with 0.75% sodium chloride to provide a 30 mg/mL solution for administration to Group 2.

During the 13 week treatment period dogs received daily topical ocular doses of GW559090 or vehicle (12 times a day) at a constant dose volume of 0.06 mL (given 6 or 12 times a day, with one hour between doses). The test article formulation or vehicle was carefully dropped into the everted lower eyelid of the left eye from a suitable distance, to prevent contact of the positive displacement pipette with the eye. The lower and upper lids were then gently held together for approximately five seconds, to prevent loss of dose and aid even distribution across the external ocular surface. The un-dosed eye was not manipulated at any time and served as a within animal untreated control site.

Instillation of the test article under the lower eyelid of the left eye up to 12 times daily at concentrations up to 50 mg/mL was well-tolerated. There were no findings considered to be attributable to local or systemic effects of the test article.

In conclusion, topical ocular administration of GW559090 to beagle dogs for 13 weeks at 30 or 50 mg/mL/occasion six times daily or 50 mg/mL/occasion 12 times daily, with one hour between doses, was well-tolerated and caused no ocular change or systemic toxicity. The No-Observed-Adverse-Effect level (NOAEL) was therefore 50 mg/mL/occasion given 12 times a day. At this dose, based on Week 13 values males and females combined, $AUC_{0-1}$ exposure was 11.2 ng·h/mL (estimated $AUC_{0-24}$ was 134 ng·h/mL); Cmax was 28.7 ng/mL.

A summary of toxicokinetic values for GW559090 from male and female dogs following ocular administration of GW559090A are shown in Table 4 and Table 5, respectively.

TABLE 4

Toxicokinetic Parameters for GW559090 from Male Dogs Following
Ocular Administration of GW559090A

| Parameter | Period | Dose of GW559090 (mg/mL) | | |
|---|---|---|---|---|
| | | $30^b$ | $50^b$ | $50^c$ |
| | | Male | | |
| $AUC_{0-1}$ ($AUC_{0-24}$) (ng · h/mL) | Day 1 | 3.82 (22.9) | 18.4 (110) | 36.6 (439) |
| | Week 4 | 2.27 (13.6) | 8.74 (52.4) | 11.8 (142) |
| | Week 13 | 3.81 (22.9) | 6.36 (38.2) | 10.2 (122) |
| $C_{max}^c$ (ng/mL) | Day 1 | 7.41 | 52.8 | 69.7 |
| | Week 4 | 5.30 | 24.2 | 23.8 |
| | Week 13 | 7.03 | 13.2 | 26.8 |
| $T_{max}^c$ (h) | Day 1 | 5.30 | 0.083 | 0.375 |
| | Week 4 | 0.25 | 0.167 | 0.25 |
| | Week 13 | 0.5 | 0.25 | 0.25 | a. After the first daily dose
b. 6 daily doses
c. 12 daily doses
NA: Not Applicable

TABLE 5

Toxicokinetic Parameters for GW559090 from Female Dogs Following
Ocular Administration of GW559090A

| Parameter | Period | Dose of GW559090 (mg/mL) | | |
|---|---|---|---|---|
| | | $30^b$ | $50^b$ | $50^c$ |
| | | Female | | |
| $AUC_{0-1}$ ($AUC_{0-24}$) (ng · h/mL) | Day 1 | 5.27 (31.6) | 8.79 (52.7) | 12.8 (153) |
| | Week 4 | 4.28 (25.7) | 5.26 (31.6) | 6.77 (81.2) |
| | Week 13 | 6.05 (36.3) | 6.64 (39.8) | 12.1 (146) |
| $C_{max}^c$ (ng/mL) | Day 1 | 12.2 | 17.0 | 21.8 |
| | Week 4 | 9.34 | 11.4 | 14.5 |
| | Week 13 | 17.5 | 17.9 | 30.5 |
| $T_{max}^c$ (h) | Day 1 | 0.5 | 0.25 | 0.5 |
| | Week 4 | 0.375 | 0.25 | 0.167 |
| | Week 13 | 0.25 | 0.167 | 0.25 | a. After the first daily dose
b. 6 daily doses
c. 12 daily doses
NA: Not Applicable Example 9. A Randomized, Double-Masked, Placebo Controlled Parallel-Group Design to Evaluate the Safety, Tolerability and Efficacy of GW559090 in Dry Eye Patients This is a two-part study. Part 1 will be conducted at one or more centers and is an open-label dose de-escalation tolerability trial of GW559090 in healthy volunteers. Upon identification of a tolerable dose, the study will move to Part 2. Part 2 is a prospective, placebo controlled, randomized, double-masked, parallel group, multi-centre study assessing the safety and efficacy of GW559090 for the treatment of dry eye disease (DED).

Part 1 will have up to two treatment arms. Up to 10 healthy volunteers will receive 50 mg/mL GW559090 TID in one eye for a period of 7 days. If this dose is tolerated in 10 patients, the study will proceed to Part 2, and a lower dose will not be explored. If the 50 mg/mL is poorly tolerated, a second cohort of 10 healthy volunteers will receive 30 mg/mL GW559090 TID in one eye for a period of 7 days. If this dose is tolerated, the study will proceed to Part 2. Evaluation of tolerability will be based upon review of physical findings and responses to the tolerability questionnaire. The study will be terminated if neither dose is tolerated. Maximum duration of participation in this phase of the protocol for an individual patient will be 22 days (14 days screening, 7 days GW559090, 1 day to follow-up).

In Part 2, approximately 90 subjects with moderate to severe DED will be entered into a placebo run-in period during which they will receive one drop of placebo TID over 14 days. After the placebo run-in period, the first approximately 76 subjects who still meet inclusion criteria and have demonstrated compliance with dosing in the run-in period will be randomized to one of two arms in 2:1 ratio (GW559090: placebo). Subjects will be randomized to either the highest tolerated dose of GW559090 (from Part 1) delivered three times a day, or a dose of placebo (vehicle) three times a day. Subjects will continue drug as assigned for up to 12 weeks. The maximum duration of participation of subjects in this phase of the protocol will be 115 days (14 days screening, 14 days placebo run-in, 84 days treatment, and 3 days to follow-up).

Part 2 of the protocol is intended to establish proof of concept in a dry eye population. Given that the efficacy observed in pre-clinical models was non-inferior to dexamethasone, it is reasonable to expect that meaningful effects will be seen on an objective physiological biomarker (corneal staining) that directly reflects epithelial integrity in the eye. A double blind randomized approach is appropriate as multiple end points are subject to reporting bias, by either the investigator or the subject. A placebo (vehicle) arm is included because prior studies have demonstrated pronounced placebo effects due in part to the lubricating effect of vehicle eye drops. A clinical result therefore cannot be assessed without accounting for this effect.

Example 10. Study to Evaluate the Safety, Tolerability and Efficacy of GW559090 in Dry Eye Patients In this study, approximately 200 subjects with moderate to severe DED will initially be screened. Approximately 120 subjects will be randomized to one of two arms in 1:1 ratio (GW559090: placebo). Subjects will be randomized to either the highest tolerated dose of GW559090 (e.g., 50 mg/mL) delivered three times a day, or a dose of placebo (vehicle) three times a day. The duration of this phase of the study will be 98-101 days (14 days placebo run-in, 84 days treatment, and, optionally, 3 days to follow-up).

Upon completion of an interim analysis, additional subjects will then be randomized into a parallel dose-ranging study. If the interim analysis reveals a strong response to TID of the highest tolerated dose, approximately 200 subjects will be randomized to one of five groups: placebo TID; 3 mg/mL TID; 30 mg/mL TID; 50 mg/mL TID; or 50 mg/mL BID. If the interim analysis reveals a moderate response to TID of the highest tolerated dose, approximately 140 subjects will be randomized to one of four groups: placebo TID; 3 mg/mL TID; 30 mg/mL TID; or 50 mg/mL TID.

REFERENCES

Chotikavanich S, de Paiva C S, Li D Q, Chen J J, Bian F, Farley W J, Pflugfelder S C. Production and Activity of Matrix Metalloproteinase-9 on the Ocular Surface Increase in Dysfunctional Tear Syndrome. *Invest Ophthalmol Vis Sci.* 2009; 50:3203-3209.

Cohen L. B., Nanau R. M., Delzor F., Neuman M. G. Biologic therapies in inflammatory bowel disease. *Translational research: the journal of laboratory and clinical medicine.* 2014; 163:533-556.

Corrales R. M., Stern M. E., de Paiva C. S., Welch J., Li D. Q., Pflugfelder S. C. Desiccating stress stimulates expression of matrix metalloproteinases by the corneal epithelium. *Invest Ophthalmol Vis Sci.* 2006; 47:3293-3302.

Coursey T. G., Bohat R., Barbosa F. L., Pflugfelder S. C., de Paiva C. S. Desiccating stress-induced chemokine expression in the epithelium is dependent on upregulation of NKG2D/RAE-1 and release of IFN-gamma in experimental dry eye. *J Immunol.* 2014; 193:5264-5272.

Coursey T. G., Gandhi N. B., Volpe E. A., Pflugfelder S. C., de Paiva C. S. Chemokine receptors CCR6 and CXCR3 are necessary for CD4(+) T cell mediated ocular surface disease in experimental dry eye disease. *PLoS One.* 2013; 8:e78508.

Cross A. H., Naismith R. T. Established and novel disease-modifying treatments in multiple sclerosis. *J Intern Med.* 2014; 275:350-363.

Cox D., Brennan M., Moran N. Integrins as therapeutic targets: lessons and opportunities. *Nat Rev Drug Discov* 2010; 9:804-20.

de Paiva C. S., Chotikavanich S., Pangelinan S. B., Pitcher J. D., Ill, Fang B., Zheng X., Ma P., Farley W. J., Siemasko K. S., Niederkorn J. Y., Stern M. E., Li D. Q., Pflugfelder S. C. IL-17 disrupts corneal barrier following desiccating stress. *Mucosal Immunol.* 2009a; 2(3):243-253.

de Paiva C. S., Corrales R. M., Villarreal A. L., Farley W., Li D. Q., Stern M. E., Pflugfelder S. C. Corticosteroid and doxycycline suppress MMP-9 and inflammatory cytokine expression, MAPK activation in the corneal epithelium in experimental dry eye. *Exp Eye Res.* 2006a; 83:526-535.

de Paiva C. S., Corrales R. M., Villarreal A. L., Farley W., Li D. Q., Stern M. E., Pflugfelder S. C. Apical corneal barrier disruption in experimental murine dry eye is abrogated by methylprednisolone and doxycycline. *Invest Ophthalmol Vis Sci.* 2006b; 47:2847-2856.

de Paiva C. S., Pangelinan S. B., Chang E., Yoon K. C., Farley W. J., Li D. Q., Pflugfelder S. C. Essential role for c-Jun N-terminal kinase 2 in corneal epithelial response to desiccating stress. *Arch Ophthalmol.* 2009b; 127:1625-1631.

de Paiva C. S., Volpe E. A., Gandhi N. B., Zhang X., Zheng X., Pitcher J. D., Ill, Farley W. J., Stern M. E., Niederkorn J. Y., Li D. Q., Flavell R. A., Pflugfelder S. C. Disruption of TGF-beta Signaling Improves Ocular Surface Epithelial Disease in Experimental Autoimmune Keratoconjunctivitis Sicca. *PLoS One.* 2011; 6:e29017. Epub 2011 Dec. 14.

Dursun D., Wang M., Monroy D., Li D. Q., Lokeshwar B. L., Stern M. E., Pflugfelder S. C. A mouse model of keratoconjunctivitis sicca. *Invest Ophthalmol Vis Sci.* 2002; 43:632-638.

Ecoiffier T., El Annan J., Rashid S., Schaumberg D., Dana R. Modulation of integrin alpha4beta1 (VLA-4) in dry eye disease. *Arch Ophthalmol.* 2008; 126:1695-1699.

Edwards J. C., Wilkinson L. S., Speight P., Isenberg D. A. Vascular cell adhesion molecule 1 and alpha 4 and beta 1 integrins in lymphocyte aggregates in Sjögren's syndrome and rheumatoid arthritis. *Ann Rheum Dis.* 1993; 52:806-811.

Goldstein M H, Tubridy K L, Agahigian J, Furfine E, Magill M, Kovalchin J, Golden K, Zarbis-Papastoitsis G, Soong F, Salapatek A M, Sternberg G, Celniker A. A Phase 2 Exploratory Study of a Novel Interleukin-1 Receptor Inhibitor (EBI-005) in the Treatment of Moderate-to-Severe Allergic Conjunctivitis. *Eye Contact Lens.* 2015; 41:145-55

Gutcher I., Donkor M. K., Ma Q., Rudensky A. Y., Flavell R. A., Li M. O. Autocrine transforming growth factor-beta1 promotes in vivo Th17 cell differentiation. *Immunity.* 2011; 34:396-408.

Hou J, Townson S A, Kovalchin J T, Masci A, Kiner O, Shu Y, King B M, Schirmer E, Golden K, Thomas C, Garcia K C, Zarbis-Papastoitsis G, Furfine E S, Barnes T M. Design of a superior cytokine antagonist for topical ophthalmic use. *Proc Natl Acad Sci USA.* 2013; 110:3913-8.

Ludwig A. The use of mucoadhesive polymers in ocular drug delivery. *Adv Drug Deliv Rev* 2005; 57:1595-639.

Luo L., Li D. Q., Doshi A., Farley W., Corrales R. M., Pflugfelder S. C. Experimental dry eye stimulates production of inflammatory cytokines and MMP-9 and activates MAPK signaling pathways on the ocular surface. *Invest Ophthalmol Vis Sci.* 2004; 45:4293-4301.

Marsh P., Pflugfelder S. C. Topical nonpreserved methylprednisolone therapy for keratoconjunctivitis sicca in Sjogren syndrome. *Ophthalmology.* 1999; 106:811-816.

Massingale M. L., Li X., Vallabhajosyula M., Chen D., Wei Y., Asbell P. A. Analysis of inflammatory cytokines in the tears of dry eye patients. *Cornea.* 2009; 28:1023-1027.

Niederkorn J. Y., Stern M. E., Pflugfelder S. C., de Paiva C. S., Corrales R. M., Gao J., Siemasko K. Desiccating Stress Induces T Cell-Mediated Sjogren's Syndrome-Like Lacrimal Keratoconjunctivitis. *J Immunol.* 2006; 176:3950-3957.

Nojima Y., Humphries M. J., Mould A. P., Komoriya A., Yamada K. M., Schlossman S. F., Morimoto C. VLA-4 meidates CD3-dependent CD4+ T cell activation via the CS1 alternatively sliced domain of fibronectin. *J Exp Med* 1990; 172:1185-92.

Pflugfelder S. C., de Paiva C. S., Li D. Q., Stern M. E. Epithelial-immune cell interaction in dry eye. *Cornea.* 2008; 27 Suppl 1:S9-11.

Pflugfelder S. C., Farley W., Luo L., Chen L. Z., de Paiva C. S., Olmos L. C., Li D. Q., Fini M. E. Matrix metalloproteinase-9 knockout confers resistance to corneal epithelial barrier disruption in experimental dry eye. *Am J Pathol.* 2005; 166:61-71.

Pflugfelder S. C., Jones D., Ji Z., Afonso A., Monroy D. Altered cytokine balance in the tear fluid and conjunctiva of patients with Sjogren's syndrome keratoconjunctivitis sicca. *Curr Eye Res.* 1999; 19:201-211.

Ravensberg A. J., Luijk B., Westers P., Hiemstra P. S., Sterk P. J., Lammers J. W., Rabe K. F. The effect of a single inhaled dose of a VLA-4 antagonist on allergen-induced airway responses and airway inflammation in patients with asthma. *Allergy.* 2006; 61:1097-1103.

Research in dry eye: report of the Research Subcommittee of the International Dry Eye WorkShop. *Ocul Surf* 2007; 5:179-193.

Schaumburg C. S., Siemasko K. F., de Paiva C. S., Pflugfelder S C, Stern M. E. Ocular Surface Antigen Presenting Cells are Necessary for Activation of Autoreactive T cells and Development of Autoimmune Lacrimal Keratoconjunctivtis. *J Immunol.* 2011; 187:3653-3662.

Sheppard J. D., Torkildsen G. L., Lonsdale J. D., D'Ambrosio F. A., Jr., McLaurin E. B., Eiferman R. A., Kennedy K. S., Semba C. P. Lifitegrast ophthalmic solution 5.0% for treatment of dry eye disease: results of the OPUS-1 phase 3 study. *Ophthalmology.* 2014; 121:475-483.

Stern M. E., Schaumburg C. S., Dana R., Calonge M., Niederkorn J. Y., Pflugfelder S. C., Autoimmunity at the ocular surface: pathogenesis and regulation. *Mucosal Immunol.* 2010; 3:425-442.

Stern M. E., Schaumburg C. S., Pflugfelder S. C. Dry eye as a mucosal autoimmune disease. *Int Rev Immunol.* 2013; 32:19-41.

Stockinger, B., Veldhoen M., Martin B. Th17 T cells: linking innate and adaptive immunity. *Semin Immunol.* 2007; 19:353-361.

Yoon K. C., de Paiva C. S., Qi H., Chen Z., Farley W. J., Li D. Q., Pflugfelder S. C. Expression of th-1 chemokines and chemokine receptors on the ocular surface of C57BL/6 mice: effects of desiccating stress. *Invest Ophthalmol Vis Sci.* 2007; 48:2561-2569.

Yoon K. C., Park C. S., You I. C., Choi H. J., Lee K. H., Im S. K., Park H. Y., Pflugfelder S. C. Expression of CXCL9, -10, -11, and CXCR3 in the tear film and ocular surface of patients with dry eye syndrome. *Invest Ophthalmol Vis Sci.* 2010; 51:643-650.

Zhang X., Schaumburg C. S., Coursey T. G., Siemasko K. F., Volpe E. A., Gandhi N. B., Li D. Q., Niederkorn J. Y., Stern M. E., Pflugfelder S. C., de Paiva C. S. CD8(+) cells regulate the T helper-17 response in an experimental murine model of Sjogren syndrome. *Mucosal Immunol.* 2014; 7:417-427.

Zhang X., Volpe E. A., Gandhi N. B., Schaumburg C. S., Siemasko K. F., Pangelinan S. B., Kelly S. D., Hayday A. C., Li D. Q., Stern M. E., Niederkorn J. Y., Pflugfelder S. C., de Paiva C. S. NK cells promote Th-17 mediated corneal barrier disruption in dry eye. *PLoS One.* 2012; 7:e36822.

Zheng X., de Paiva C. S., Rao K., Li D. Q., Farley W. J., Stern M., Pflugfelder S. C. Evaluation of the transforming growth factor-beta activity in normal and dry eye human tears by CCL-185 cell bioassay. *Cornea* 2010; 29:1048-1054.

Zoukhri D. Effect of inflammation on lacrimal gland function. *Exp Eye Res* 2006; 82:885-98.

EXEMPLARY EMBODIMENTS

A1. A pharmaceutical composition comprising a compound of formula I which is

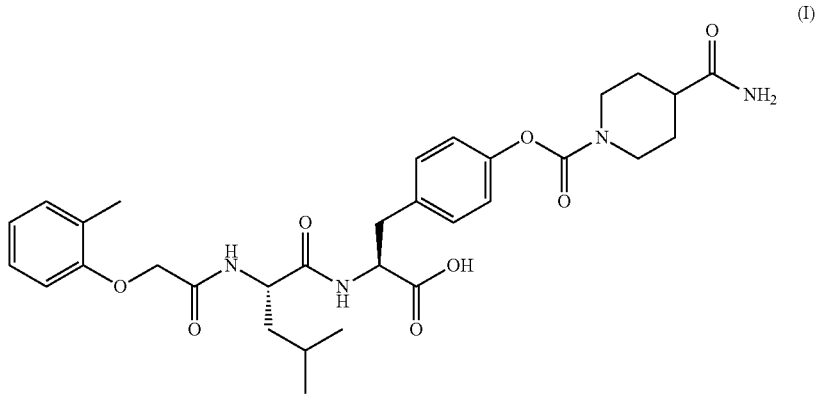 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or any pharmaceutically acceptable isomer, hydrate, anhydride, solvate, ester, salt form, free acid or base, prodrug, complex, conjugate, or polymorph thereof, and one or more pharmaceutically acceptable excipients.

A2. The pharmaceutical composition of embodiment A1, wherein the composition is applied topically.

A3. The pharmaceutical composition of embodiment A1, wherein the composition is applied to the conjunctival sac or to the eyelid.

A4. The pharmaceutical composition of embodiment A1, wherein the composition is applied subconjunctivally, intracamerally, intravitreally, subtenon, subretinally, subchoroidally, or suprachoroidally.

A5. The pharmaceutical composition of embodiments A2, A3 or A4, which is useful for treating an ocular inflammatory condition.

A6. The pharmaceutical composition of any of the preceding embodiments, wherein the composition is applied in the form of an eye drop, spray or mist.

A7. The pharmaceutical composition of any of the preceding embodiments, wherein the composition is applied with an insert or other delivery device.

A8. A method for treatment of an ocular inflammatory condition in a mammal/human in need thereof comprising administering to said mammal/human a therapeutically effective amount of a compound of formula I which is or any pharmaceutically acceptable isomer, hydrate, anhydride, solvate, ester, salt form, free acid or base, prodrug, complex, conjugate, or polymorph thereof, and one or more pharmaceutically acceptable excipients.

A9. The method of embodiment A8, wherein the composition is applied topically.

A10. The method of embodiment A8, wherein the composition is applied to the conjunctival sac or to the eyelid.

A11. The method of embodiment A8, wherein the composition is applied subconjunctivally, intracamerally, intravitreally, subtenon, subretinally, subchoroidally, or suprachoroidally.

A12. The method of any of the preceding embodiments, wherein the composition is applied in the form of an eye drop, spray or mist.

A13. The method of any of the preceding embodiments, wherein the composition is applied with an insert or other delivery device.

A14. A pharmaceutical composition comprising a compound of formula I which is

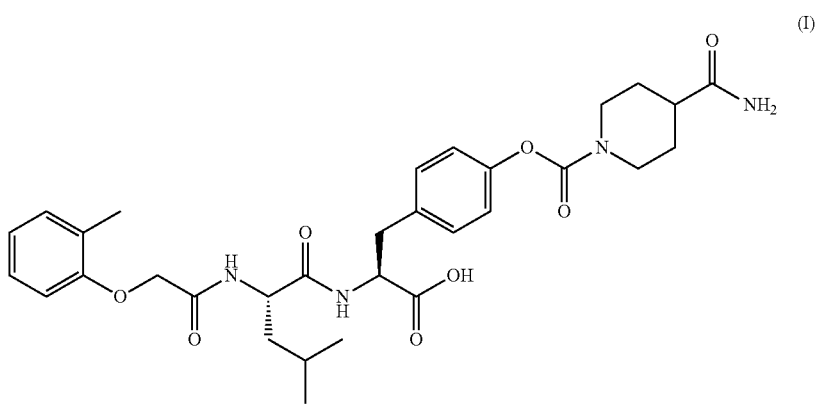 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

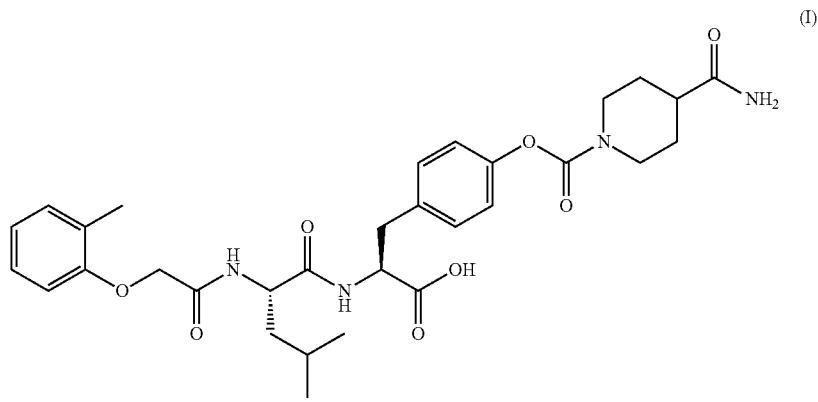 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or any pharmaceutically acceptable isomer, hydrate, anhydride, solvate, ester, salt form, free acid or base, prodrug, complex, conjugate, or polymorph thereof, and one or more pharmaceutically acceptable excipients, for use in the treatment of an ocular inflammatory condition.

A15. A method for treating an ocular inflammatory condition in a mammal/human in need thereof by blocking the migration of antigen-presenting cells to the lymph nodes, which method comprises administering to said mammal/human a therapeutically effective amount of compound of formula I which is

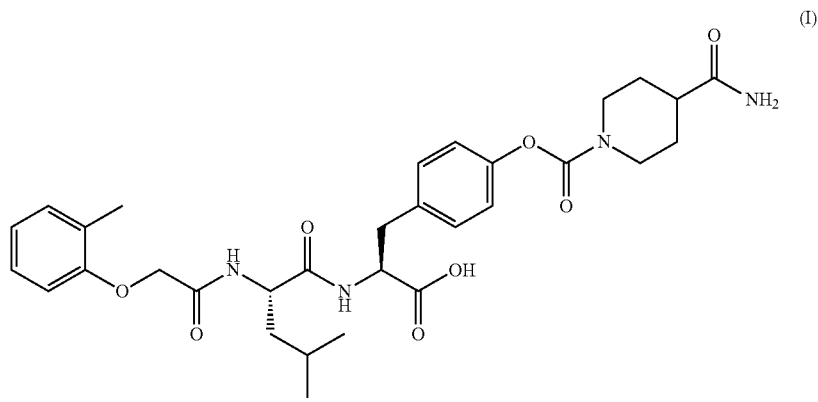 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or any pharmaceutically acceptable isomer, hydrate, anhydride, solvate, ester, salt form, free acid or base, prodrug, complex, conjugate, or polymorph thereof, and one or more pharmaceutically acceptable excipients.

A16. A method for treatment of an ocular inflammatory condition in a mammal/human in need thereof comprising administering to said mammal/human a therapeutically effective amount of: (a) a pharmaceutical composition comprising a compound of formula I which is

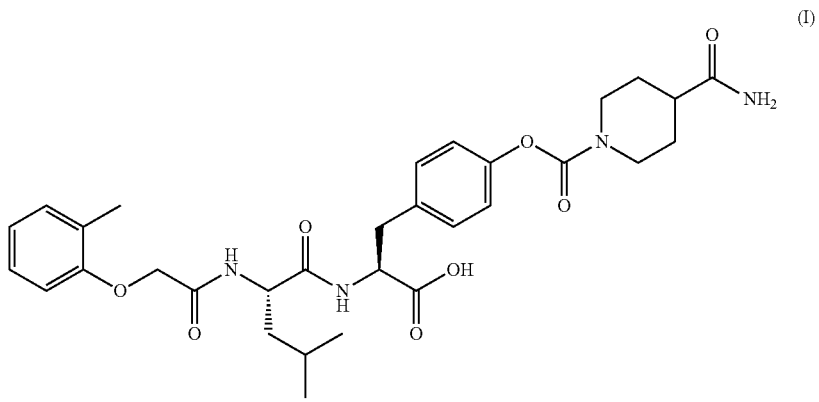 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or any pharmaceutically acceptable isomer, hydrate, anhydride, solvate, ester, salt form, free acid or base, prodrug, complex, conjugate, or polymorph thereof; and (b) cyclosporin A, and one or more pharmaceutically acceptable excipients.

A17. A method for treatment of an ocular inflammatory condition in a mammal/human in need thereof comprising administering to said mammal/human a therapeutically effective amount of: (a) a pharmaceutical composition comprising a compound of formula I which is

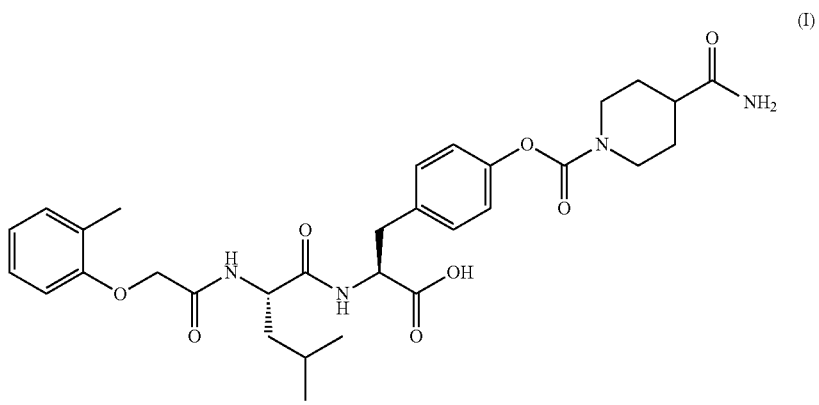 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or any pharmaceutically acceptable isomer, hydrate, anhydride, solvate, ester, salt form, free acid or base, prodrug, complex, conjugate, or polymorph thereof; and (b) a topical steroid selected from the group consisting of dexamethasone base and phosphate, difluprednate, fluocinolone, fluorometholone base and acetate, loteprednol, prednisolone acetate and phosphate, rimexolone, and triamcinolone acetonide, and one or more pharmaceutically acceptable excipients.

A18. A method for treatment of an ocular inflammatory condition in a mammal/human in need thereof comprising administering to said mammal/human a therapeutically effective amount of: (a) a pharmaceutical composition comprising a compound of formula I which is

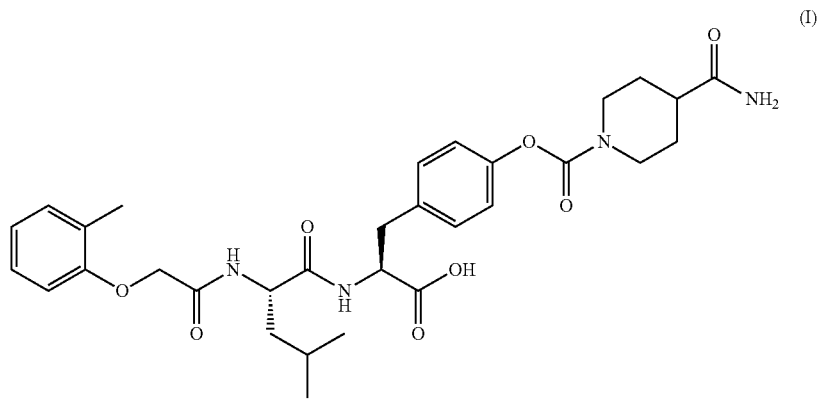 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or any pharmaceutically acceptable isomer, hydrate, anhydride, solvate, ester, salt form, free acid or base, prodrug, complex, conjugate, or polymorph thereof; and (b) a non-steroidal anti-inflammatory drug selected from the group consisting of bromfenac, diclofenac, flurbiprofen, ketorolac, and nepafenac, and one or more pharmaceutically acceptable excipients.

A19. A method for treatment of an ocular inflammatory condition in a mammal/human in need thereof comprising administering to said mammal/human a therapeutically effective amount of: (a) a pharmaceutical composition comprising a compound of formula I which is

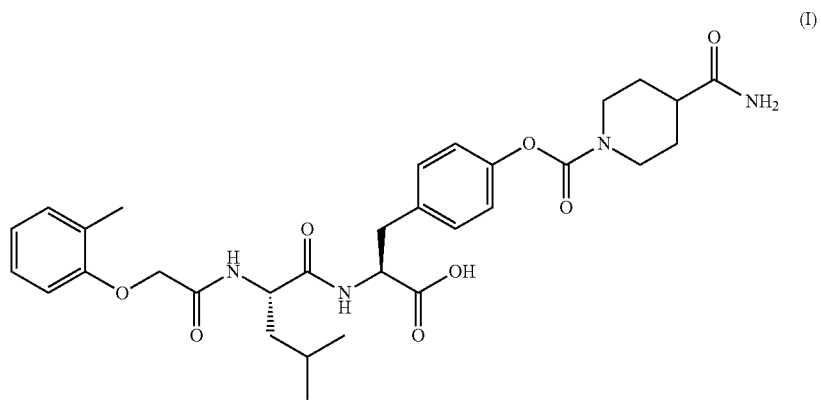 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or any pharmaceutically acceptable isomer, hydrate, anhydride, solvate, ester, salt form, free acid or base, prodrug, complex, conjugate, or polymorph thereof; and (b) an LFA-1 integrin antagonist, and one or more pharmaceutically acceptable excipients.

A20. The method of embodiment A19, wherein the LFA-1 integrin antagonist is lifitegrast.

A21. The method of embodiments A15, A16, A17, A18, A19, or A20, wherein the composition is applied topically in the form of an eye drop, spray or mist.

A22. Use of compound of formula I which is

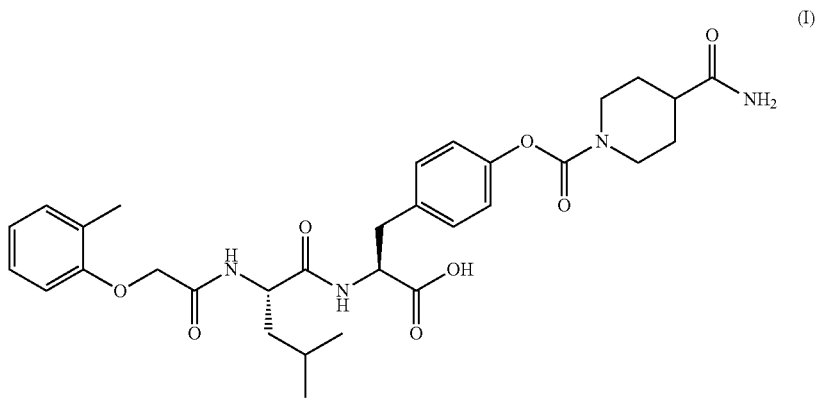 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or any pharmaceutically acceptable isomer, hydrate, anhydride, solvate, ester, salt form, free acid or base, prodrug, complex, conjugate, or polymorph thereof, and one or more pharmaceutically acceptable excipients, in the manufacture of a medicament for the treatment of an ocular inflammatory condition.

A23. The pharmaceutical composition, method, or use of any of the preceding embodiments, wherein the ocular inflammatory condition is dry eye disease, non-infectious uveitis (e.g., anterior, intermediate, posterior, or pan-uveitis), non-infectious conjunctivitis, iritis, or scleritis.

A24. The pharmaceutical composition, method, or use of any of the preceding embodiments, wherein the ocular inflammatory condition is dry eye disease.

What is claimed is:

1. A method of treatment, comprising,
ocularly administering a pharmaceutical composition comprising an effective amount of a compound of formula I

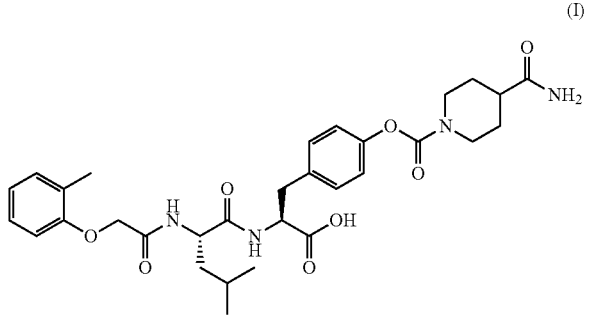 [SMILES: Cc1ccccc1OCC(=O)N[C@@H](CC(C)C)C(=O)N[C@@H](Cc1ccc(OC(=O)N2CCC(C(N)=O)CC2)cc1)C(=O)O]

or a pharmaceutically acceptable salt, ester, hydrate, solvate, polymorph, optical isomer, racemate, diastereoisomer or enantiomer thereof at a dosing suitable to primarily act locally, to a human subject suffering from an ocular inflammatory condition,
wherein the pharmaceutical composition is administered with an individual dose of the compound in the range of from about 0.1 mg to about 2 mg, in each affected eye.

2. The method of claim 1, wherein the ocular inflammatory condition is selected from the group consisting of dry eye disease, noninfectious uveitis, non-infectious conjunctivitis, iritis, and scleritis.

3. The method of claim 1, wherein the pharmaceutically acceptable salt is a potassium salt.

4. The method of claim 1, wherein the pharmaceutical composition is administered in a volume between about 10 µL and about 100 µL.

5. The method of claim 4, wherein the pharmaceutical composition contains between about 10 mg/mL and about 100 mg/mL of the compound of formula I or the pharmaceutically acceptable salt, hydrate, solvate, polymorph, optical isomer, racemate, diastereoisomer or enantiomer thereof.

6. The method of claim 1, wherein the pharmaceutical composition is administered with an individual dose of the compound in the range from about 1 mg to about 2 mg, in each affected eye.

7. The method of claim 1, wherein the pharmaceutical composition is administered with an individual dose of the compound in the range from about 0.5 mg to about 2 mg, in each affected eye.

8. The method of claim 1, wherein the pharmaceutical composition is administered with an individual dose of the compound that is about 0.5 mg, about 0.6 mg, about 0.8 mg, about 1.0 mg, about 1.2 mg, about 1.4 mg, about 1.6 mg, about 1.8 mg, or about 2.0 mg, in each affected eye.

9. The method of claim 1, wherein the pharmaceutical composition is administered with an individual dose of the compound at about 1.4 mg, in each affected eye.

10. The method of claim 1, wherein the pharmaceutical composition is administered with an individual dose of the compound at about 0.8 mg, in each affected eye.

11. The method of claim 1, wherein the pharmaceutical composition is administered topically.

12. The method of claim 1, wherein the pharmaceutical composition is administered subconjunctivally, intracamerally, intravitreally, subtenon, subretinally, subchoroidally, or suprachoroidally.

13. The method of claim 1, wherein the pharmaceutical composition is administered in the form of an eye drop, gel, ointment, spray, or mist.

14. The method of claim 1, further comprising co-administering one or more additional therapeutic agents selected from the group consisting of (a) cyclosporin A; (b) a steroid selected from the group consisting of dexamethasone base, dexamethasone phosphate, difluprednate, fluocinolone, fluorometholone base, fluorometholone acetate, loteprednol, prednisolone acetate, prednisolone phosphate, rimexolone, and triamcinolone acetonide; (c) a non-steroidal anti-inflammatory agent selected from the group consisting of bromfenac, diclofenac, flurbiprofen, ketorolac, and nepafenac; and (d) an LFA-1 antagonist.

15. The method of claim 14, wherein the co-administration is in a same or separate pharmaceutical composition.

* * * * *